(12) United States Patent
Wei et al.

(10) Patent No.: US 11,655,240 B1
(45) Date of Patent: *May 23, 2023

(54) CRYSTAL FORM OF COMPOUND AND FUMARIC ACID, PHARMACEUTICAL COMPOSITION AND METHOD FOR TREATING CORONAVIRUS-INDUCED DISEASES

(71) Applicants: BEIJING GRAND JOHAMU PHARMACEUTICAL COMPANY, LTD., Beijing (CN); NANJING GRITPHARMACO., LTD., NanJing (CN)

(72) Inventors: Weiye Wei, Beijing (CN); Jiannan Yang, Beijing (CN); Xiaotao Wu, Beijing (CN); Taotao Zhao, Beijing (CN); Hao Wang, Beijing (CN); Chao Li, Beijing (CN); Lei Qu, Beijing (CN); Bin Wang, Beijing (CN)

(73) Assignees: BEIJING GRAND JOHAMU PHARMACEUTICAL COMPANY, LTD., Beijing (CN); NANJING GRITPHARMACO., LTD., Nanjing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/964,389

(22) Filed: Oct. 12, 2022

(30) Foreign Application Priority Data

May 10, 2022 (CN) .......................... 202210500296.8
Jun. 9, 2022 (CN) .......................... 202210644417.6
Sep. 15, 2022 (CN) .......................... 202211119888.1

(51) Int. Cl.
*C07D 403/14* (2006.01)
*A61P 31/14* (2006.01)
*A61K 9/20* (2006.01)

(52) U.S. Cl.
CPC .......... *C07D 403/14* (2013.01); *A61K 9/2009* (2013.01); *A61K 9/2013* (2013.01); *A61K 9/2054* (2013.01); *A61K 9/2059* (2013.01); *C07B 2200/13* (2013.01)

(58) Field of Classification Search
CPC ............................. C07D 403/14; A61P 31/14
See application file for complete search history.

(56) References Cited

U.S. PATENT DOCUMENTS

| 2021/0346409 A1 | 11/2021 | Alexander et al. |
| 2022/0009903 A1 | 1/2022 | Vandyck et al. |

FOREIGN PATENT DOCUMENTS

| CN | 101214242 A | 7/2008 |
| CN | 101584696 A | 11/2009 |
| CN | 102088972 A | 6/2011 |
| CN | 106994121 A | 8/2017 |
| CN | 113198019 A | 8/2021 |
| CN | 113521289 A | 10/2021 |
| CN | 114591304 A | 6/2022 |
| CN | 115038696 A | 9/2022 |
| WO | 2021183774 A1 | 9/2021 |
| WO | 2022035911 A1 | 9/2021 |
| WO | 2022035911 A2 | 2/2022 |
| WO | 2022053993 A2 | 3/2022 |

OTHER PUBLICATIONS

Chinese First Office Action and First Search Report dated Jun. 14, 2022 issued in CN 202210500296.8.
Chinese First Office Action and First Search Report dated Jul. 14, 2022 issued in CN 202210644417.6.
Chinese Grant Notice dated Jun. 18, 2022 issued in CN 202210500296.8.
Chinese Grant Notice and Supplementary Search dated Aug. 31, 2022 issued in CN 202210644417.6.
Zhang Libin et al., "Control and Application of Crystal Size of Cefaclor", Chemical and Pharmaceutical Engineering (2022), vol. 43, No. 2, pp. 33-37.
Jennifer L.McKimm-Breschkin et al., "COVID-19, Infuenza and RSV: Surveillance-informed prevention and treatment—Meeting report from an isirv-WHO virtual conference", Antiviral Research 197 (2022), 105227, pp. 1-18.

(Continued)

*Primary Examiner* — Samira J Jean-Louis
(74) *Attorney, Agent, or Firm* — Scully, Scott, Murphy & Presser, P.C.

(57) ABSTRACT

The present disclosure provides a crystal form of a compound and fumaric acid, an active pharmaceutical ingredient and a pharmaceutical composition containing the same, and a method for treating coronavirus-induced diseases a using the same. In particular, the crystal form of the present disclosure comprises the compound of Formula (I) and fumaric acid, and the X-ray powder diffraction pattern of the crystal form obtained using Cu-Kα radiation includes at least three peaks selected from the group consisting of: 0.94°±0.2° 2θ, 19.06°±0.2° 2θ, 23.50°±0.2° 2θ, and 24.66°±0.2° 2θ. The crystal form of the present disclosure has a high purity, good stability, and a high melting point.

Formula (I)

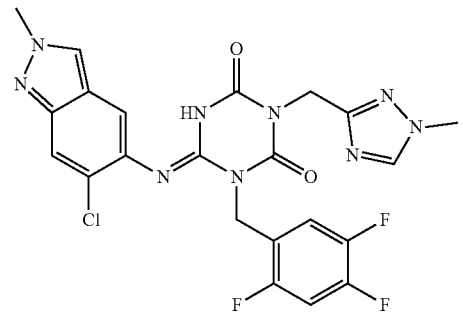

20 Claims, 5 Drawing Sheets

(56) References Cited

OTHER PUBLICATIONS

Joel D. A. Tyndall, "S-217622, a 3CL Protease Inhibitor and Clinical Candidate for SARSCoV-2", J. Med. Chem. (2022), vol. 65, pp. 6496-6498.
Yuto Unoh et al., "Discovery of S-217622, a Noncovalent Oral SARS-CoV-2 3CL Protease Inhibitor Clinical Candidate for Treating COVID-19", J. Med. Chem. (2022), vol. 65, pp. 6499-6512.
First Office Acton dated Nov. 8, 2022 received in Chinese Patent Application No. CN 202211119888.1.
Notice of Decision of Granting Patent Right for Invention dated Nov. 28, 2022 received in Chinese Patent Application No. CN 202211119888.1.

Particle size classification (μm)

CRYSTAL FORM OF COMPOUND AND FUMARIC ACID, PHARMACEUTICAL COMPOSITION AND METHOD FOR TREATING CORONAVIRUS-INDUCED DISEASES

FIELD

The present disclosure relates to the medical field, specifically, to a crystal form of a specific compound and fumaric acid, an active pharmaceutical ingredient and a pharmaceutical composition containing the same and/or a method for treating coronavirus-induced diseases using the same.

BACKGROUND

Due to the outbreak of Severe Acute Respiratory Syndrome (SARS) in 2003 and Middle East Respiratory Syndrome (MERS) in 2012, coronaviruses have gradually become a research hotspot in the field of virology. The Corona Virus Disease 2019 (COVID-19) is a new acute respiratory infectious disease caused by SARS-CoV-2 (also known as 2019-nCoV), which, ever since its outbreak in December, 2019, has caused more than 200 million infections and more than 4 million deaths, has now become a major global public health event, and has a significant impact on the global society and economy. At present, in view of the severe situation of the epidemic, practical and effective treatment methods are urgently needed.

Some compounds with therapeutic potential for diseases caused by coronaviruses (especially 2019-nCoV) have been disclosed in the art. However, at the current stage, there is still a need for a pharmaceutical composition for the treatment of diseases caused by coronaviruses (especially 2019-nCoV) to meet the urgent needs of clinical treatment.

SUMMARY

In view of the above problems existing in the art, the present disclosure provides technical solutions to solve the above problems.

In a first aspect of the present disclosure, a crystal form of a compound of Formula (I) and fumaric acid is provided. In other words, the first aspect of the present disclosure provides a crystal form comprising a compound of Formula (I) and fumaric acid, characterized in that an X-ray powder diffraction pattern of the crystal form obtained by using Cu-Kα radiation includes at least three peaks selected from a group consisting of 10.94°±0.2° 2θ, 19.06°±0.2° 2θ, 23.50°±0.2° 2θ, and 24.66°±0.2° 2θ.

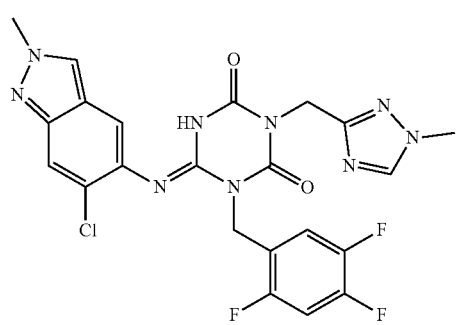

Formula (I)

In a second aspect of the present disclosure, the present disclosure provides an active pharmaceutical ingredient containing the crystal form of the first aspect, the active pharmaceutical ingredient satisfying at least one of the following conditions: (1) a particle size $D_{90}$ of the active pharmaceutical ingredient ranges from about 5 μm to about 60 μm; and (2) a particle size $D_{50}$ of the active pharmaceutical ingredient does not exceed about 30 μm.

In a third aspect of the present disclosure, the present disclosure provides a pharmaceutical composition comprising: an active ingredient, the active ingredient being the crystal form of the first aspect, a mixture of the crystal form and an amorphous form of the compound of Formula (I) and fumaric acid, or the active pharmaceutical ingredient of the second aspect; and physiologically or pharmaceutically acceptable excipient(s) including one or more selected from a group consisting of filler(s), disintegrant(s), lubricant(s), binder(s), and glidant(s).

In a fourth aspect of the present disclosure, the present disclosure provides a method for treating coronavirus-induced diseases, including: administering the pharmaceutical composition of the third aspect to a subject.

The crystal form of the compound of Formula (I) and fumaric acid of the present disclosure has a high purity (>98 area % HPLC) and good stability (including stability under the conditions of light irradiation, high temperature, and high humidity; and stability in the accelerated stability test) and has a high melting point. Therefore, the active pharmaceutical ingredient containing the crystal form of the present disclosure is conducive to storage at room temperature and quality control, can effectively extend the shelf life of drugs comprising the same, and can meet the pharmaceutical requirements of production, processing, transportation, and storage.

In addition, the inventors found through creative research that the pharmaceutical composition described herein has the function of inhibiting coronavirus, especially 2019-nCoV, and has good potential therapeutic effect in the treatment of diseases caused by 2019-nCoV. In addition, the pharmaceutical compound of the present disclosure has a high dissolution, a high dissolution rate, and/or high stability. Moreover, the pharmaceutical composition of the present disclosure is suitable for preparing oral preparations, especially oral solid preparations such as tablets, suitable for industrialized large-scale production, and the obtained products have stable and reliable quality, and have good clinical application value.

Additional aspects and advantages of the present disclosure will be set forth, in part, from the following description, and in part will be apparent from the following description, or learned by practice of the present disclosure.

DESCRIPTION OF EMBODIMENTS

Figure 1:
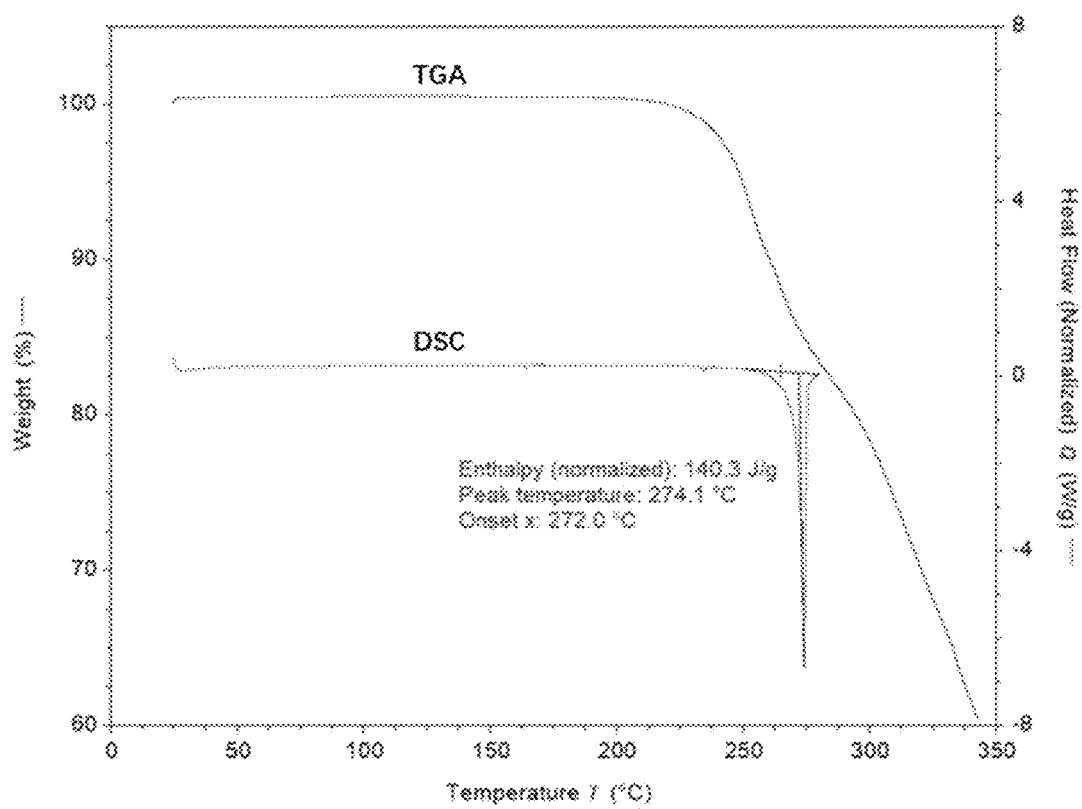
FIG. 1 shows a differential scanning calorimetry (DSC) spectrum and a thermogravimetric analysis (TGA) spectrum of the crystal form A of the compound of Formula (I) and fumaric acid.

The technical solutions in the embodiments of the present disclosure will be clearly and completely described below with reference to the accompanying drawings in the examples of the present disclosure. The described embodiments should not be regarded as limitative of the present disclosure, and all other embodiments obtained by those skilled in the art without creative work fall within the protection scope of the present disclosure.

Unless otherwise defined, all terms used herein have the same meaning as commonly understood by those skilled in the art to which the present disclosure belongs. The terms used herein are only for the purpose of describing the embodiments of the present disclosure, and are not intended to limit the present disclosure. Before further detailed description of the embodiments of the present disclosure, the nouns and terms involved in the embodiments of the present disclosure are first described. The following explanations apply for the nouns and terms involved in the embodiments of the present disclosure.

Unless expressly stated otherwise, numerical ranges throughout this specification include any subrange therein and any numerical value incremented by the smallest subunit of the value given therein. Unless expressly stated otherwise, numerical values throughout this specification represent approximate measures or limitations of ranges of embodiments including minor deviations from the given values, having about the recited value, and having the recited exact value. Except for the examples provided at the end of the detailed description, all numerical values of parameters (e.g., quantities or conditions) herein (including the appended claims) should in all instances be understood as modified by the term "about", regardless of whether the term "about" is actually present before the value. "About" means that the stated value allows for some imprecision (some approximation in the value; approximately or reasonably close to the value; approximately). If the imprecision provided by the term "about" is not understood as this ordinary meaning in the art, "about" as used herein represents at least variations that can be produced by ordinary methods for measuring and using these parameters. For example, the term "about" is generally expressed as +/−10% of the stated value, e.g., +/−5%, +/−4%, +/−3%, +/−2%, +/−1%, or +/−0.5% of the stated value.

In the present disclosure, the relative humidity is expressed as RH, which means a percentage of a water vapor content (water vapor partial pressure) in a gas (usually air) to a water vapor content of saturated water vapor (saturated water vapor pressure) in the same air at the same temperature.

As used herein, the term "physiologically or pharmaceutically acceptable excipient" refers to an excipient that does not cause significant irritation to organisms and does not hinder the biological activity and properties of the administrated active ingredient such as the crystal form of the compound and fumaric acid of the present disclosure.

The physiologically acceptable or pharmaceutically acceptable excipient to be mixed with the crystal form of the compound and fumaric acid of the present disclosure to form the pharmaceutical composition may depend on the intended route of administration of the pharmaceutical composition.

The crystal form of the compound and fumaric acid of the present disclosure may have systemic and/or local activity. For this purpose, it may be administered in a suitable manner, for example by an oral, parenteral, pulmonary, nasal, sublingual, lingual, buccal, rectal, vaginal, dermal, transdermal, conjunctival, or auricular route of administration or as an implant or stent.

For these routes of administration, the crystal form of the compound and fumaric acid of the present disclosure can be administered in a suitable administration form.

For example, for oral administration, the crystal form of the compound and fumaric acid of the present disclosure can be formulated into dosage forms known in the art for rapid and/or sustained release delivery, e.g., tablets (uncoated or coated tablets, for example, having enteric or controlled release coatings with delayed dissolution or insolubility), orally disintegrating tablets, wafers, lyophylisates, capsules (e.g., hard or soft gelatin capsules), sugar-coated tablets, granules, pills, powders, emulsions, suspensions, aerosols, or solutions. According to the embodiments of the present disclosure, the crystal form of the compound and fumaric acid of the present disclosure may be incorporated in a crystal form and/or a mixture of a crystal form and an amorphous form and/or a dissolved form into the dosage forms.

According to embodiments of the present disclosure, parenteral administration can be accomplished by avoiding absorption steps (e.g., intravenous, intraarterial, intracardiac, intraspinal, or intralumbar administration) or including absorption steps (e.g., intramuscular, subcutaneous, intradermal, transdermal, or intraperitoneal administration). Administration forms suitable for parenteral administration are especially injection and infusion preparations in the form of solutions, suspensions, emulsions, lyophilisates, or sterile powders.

As used herein, the term "subject" refers to animals, including but not limited to primates (e.g., human beings), monkeys, cows, pigs, sheep, goats, horses, dogs, cats, rabbits, rats, or mice. Specifically, the subject is 0 year old or older, 1 year old or older, 2 years old or older, 4 years old or older, 5 years old or older, 10 years old or older, 12 years old or older, 13 years old or older, 15 years old or older, 16 years old or older, 18 years old or older, 20 years old or older, 25 years old or older, 30 years old or older, 35 years old or older, 40 years old or older, 45 years old or older, 50 years old or older, 55 years old or older, 60 years old or older, 65 years old or older, 70 years old or older, 75 years old or older, 80 years old or older, 85 years old or older, 90 years old or older, 95 years old or older, 100 years old or older, or 105 years old or older.

As used in the present disclosure, the term "coronavirus" belongs to the genus Coronavirus in the family Coronaviridae. A variant of the coronavirus is the pathogen that causes SARS. Coronaviruses include but are not limited to 2019-nCoV or SARS-CoV-2 which caused the Corona Virus Disease 2019 (COVID-19), HCoV-229E, HCoV-OC43, HCoV-NL63, HCoV-HKU1, SARS-CoV that caused the Severe Acute Respiratory Syndrome, and MERS-CoV that caused Middle East Respiratory Syndrome. The diseases caused by coronaviruses are mainly respiratory infections, including the Severe Acute Respiratory Syndrome (SARS).

As used in the present disclosure, the term "2019-nCoV" refers to SARS-CoV-2 (severe acute respiratory syndrome coronavirus 2) published by the International Committee on Taxonomy of Viruses in February 2020. In the present disclosure, SARS-CoV-2 has the same meaning as 2019-nCoV, and it also includes all variant strains of 2019-nCoV, such as all variant strains included in NCBI or GISAID (Global Initiative for Sharing Influenza Data), especially including important variants with strong transmissibility, pathogenicity, or immune escape, such as Alpha, Beta, Gamma, Delta, Eta, Iota, Kappa or Lambda variants designated by WHO, and important variants to be designated subsequently.

In the present disclosure, the term "free base of the active ingredient" refers to the compound of Formula (I) described in the present disclosure.

In the present disclosure, the compound of Formula (I) is a compound with the following structure,

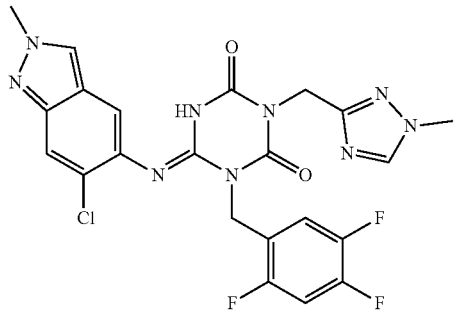

Formula (I)

namely, (6E)-6-[(6-chloro-2-methyl-2H-indazol-5-yl)imino]-3-[(1-methyl-1H-1,2,4-triazol-3-yl)methyl]-1-[(2,4,5-trifluorophenyl)methyl]-1,3,5-triazine-2,4-dione.

The compound of the present disclosure may be present in isomer(s), e.g., stereoisomeric forms (enantiomers, diastereomers), depending on the structure thereof. Accordingly, the present disclosure relates to enantiomers or diastereomers and respective mixtures thereof. Stereoisomerically pure components can be separated from the mixtures of such enantiomers and/or diastereomers by a known manner.

When the compound of the present disclosure is present as optical isomer(s), the pharmaceutical composition provided herein generally includes an optical isomer in a substantially pure form.

The present disclosure covers all tautomeric forms of the compound.

Furthermore, the compound of the present disclosure may be present in a free form, e.g., as a free base or as a free acid or as a zwitterion, or may be present in the form of a salt. The salt may be any salt commonly used in pharmacy, organic or inorganic addition salt, especially any physiologically acceptable organic or inorganic addition salt.

For the purposes of the present disclosure, the term "solvate" refers to those forms of complexes of the compound that are formed in solid or liquid forms with solvent molecule(s) through coordination. Hydrate is a specific form of solvate in which the compound coordinates with water. Within the scope of the present disclosure, hydrates are preferred as solvates.

The present disclosure also includes all suitable isotopic variants of the compound of the present disclosure. Isotopic variants of the compound of the present disclosure are defined as compounds in which at least one atom is replaced by an atom having the same atomic number but an atomic mass different from that usually or predominantly found in nature. Examples of isotopes that can be incorporated into the compound of the present disclosure include isotopes of hydrogen, carbon, nitrogen, oxygen, phosphorus, sulfur, fluorine, chlorine, bromine, and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I, and $^{131}$I. Certain isotopic variants of the compound of the present disclosure (e.g., those incorporated with one or more radioactive isotopes such as $^3$H or $^{14}$C) are useful in the study of drug and/or matrix tissue distribution. Tritium labels and carbon-14 (i.e., $^{14}$C) isotopes are particularly preferred due to their ease of preparation and detectability. Furthermore, replacement with isotopes such as deuterium may provide certain therapeutic advantages resulting from greater metabolic stability, such as increased in vivo half-life or reduced dosage demands, and may therefore be preferred in certain circumstances. Isotopic variants of the compound described in the present disclosure can generally be prepared by conventional procedures known to those skilled in the art, using appropriate isotopic variants of appropriate reagents.

Crystal Form

Unless otherwise specified, in the present disclosure, the crystal form comprising the compound of Formula (I) and fumaric acid is also called "crystal form A of the compound of Formula (I) and fumaric acid" or "crystal form of the compound of Formula (I) and fumaric acid". It should be noted that the expression "comprising the compound of Formula (I) and fumaric acid" used herein does not restrict the existence forms of the compound of Formula (I) and fumaric acid in any way. The compound of Formula (I) and fumaric acid can be bound in the form of non-covalent bond(s), for example, through a binding force such as ionic bond(s), van der Waals force(s), or π-π stacking interaction; or in the form of covalent bonds, for example, through a binding force such as hydrogen bond(s).

In a first aspect of the present disclosure, the present disclosure provides the following embodiments and any combination thereof.

According to an embodiment of the present disclosure, the crystal form of the compound of Formula (I) and fumaric acid may be an anhydrate or a hydrate (e.g., which may have one or two water molecules of crystallization).

The X-ray powder diffraction pattern, represented by 2θ value±0.2°, of the crystal form of the compound of Formula (I) and fumaric acid obtained by using Cu-Kα radiation includes any three characteristic diffraction peaks selected from the group consisting of 10.94, 19.06, 23.50, and 24.66. According to an embodiment of the present disclosure, the X-ray powder diffraction pattern, represented by 2θ value±0.2°, of the crystal form of the compound of Formula (I) and fumaric acid obtained by using Cu-Kα radiation may further includes any one or more characteristic diffraction peaks selected from the group consisting of 9.5, 13.81, 18.61, 22.59, and 23.8, preferably further includes any one or more characteristic diffraction peaks selected from the group consisting of 7.81, 10.14, 11.50, 11.93, and 12.31, preferably further includes any one or more characteristic diffraction peaks selected from the group consisting of 14.73, 20.87, 21.49, 21.97, and 25.39, and further preferably, includes the characteristic diffraction peaks at 10.94, 19.06, 23.50, 24.66, 9.5, 13.81, 18.61, 22.59, and 23.8.

In other words, the X-ray powder diffraction pattern of the crystal form obtained by using Cu-Kα radiation includes at least three characteristic diffraction peaks selected from the group consisting of 10.94°±0.2° 2θ, 19.06°±0.2° 2θ, 23.50°±0.2° 2θ, and 24.66°±0.2° 2θ. According to an embodiment of the present disclosure, the X-ray powder diffraction pattern further includes at least one characteristic diffraction peak selected from the group consisting of 9.5°±0.2° 2θ, 13.81°±0.2° 2θ, 18.61°±0.2° 2θ, 22.59°±0.2° 2θ, and 23.8°±0.2° 2θ. According to an embodiment of the present disclosure, the X-ray powder diffraction pattern further includes at least one characteristic diffraction peak selected from the group consisting of 7.81°±0.2° 2θ, 10.14°±0.2° 2θ, 11.50°±0.2° 2θ, 11.93°±0.2° 2θ, and 12.31°±0.2° 2θ. According to an embodiment of the present disclosure, the X-ray powder diffraction pattern of the crystal form further includes at least one characteristic diffraction peak selected from the group consisting of 14.73°±0.2° 2θ, 20.87°±0.2° 2θ, 21.49°±0.2° 2θ, 21.97°±0.2° 2θ, and 25.39°±0.2° 2θ. According to an embodiment of the present disclosure, the X-ray powder diffraction pattern includes at least 9 characteristic diffraction peaks selected from the group consisting of 10.94°±0.2° 2θ, 19.06°±0.2° 2θ, 23.50°±0.2° 2θ, 24.66°±0.2° 2θ, 9.5°±0.2° 2θ, 13.81°±0.2° 2θ, 18.61°±0.2° 2θ, 22.59°±0.2° 2θ, 23.8°±0.2° 2θ, 7.81°±0.2° 2θ, 10.14°±0.2° 2θ, 11.50°±0.2° 2θ, 11.93°±0.2° 2θ, 12.31°±0.2° 2θ, 14.73°±0.2° 2θ, 20.87°±0.2° 2θ, 21.49°±0.2° 2θ, 21.97°±0.2° 2θ, and 25.39°±0.2° 2θ. According to an embodiment of the present disclosure, the X-ray powder diffraction pattern includes the following characteristic diffraction peaks: 10.94°±0.2° 2θ, 19.06°±0.2° 2θ, 23.50°±0.2° 2θ, 24.66°±0.2° 2θ, 9.5°±0.2° 2θ, 13.81°±0.2° 2θ, 18.61°±0.2° 2θ, 22.59°±0.2° 2θ, and 23.8°±0.2° 2θ. According to an embodiment of the present application, the X-ray powder diffraction pattern includes the following characteristic diffraction peaks: 5.98°±0.2° 2θ, 7.81°±0.2° 2θ, 9.50°±0.2° 2θ, 10.14°±0.2° 2θ, 10.94°±0.2° 2θ, 11.50°±0.2° 2θ, 11.93°±0.2° 2θ, 12.31°±0.2° 2θ, 13.35°±0.2° 2θ, 13.81°±0.2° 2θ, 14.73°±0.2° 2θ, 15.13°±0.2° 2θ, 15.59°±0.2° 2θ, 16.35°±0.2° 2θ, 17.09°±0.2° 2θ, 17.57°±0.2° 2θ, 17.94°±0.2° 2θ, 18.07°±0.2° 2θ, 18.61°±0.2° 2θ, 19.06°±0.2° 2θ, 19.49°±0.2° 2θ, 19.82°±0.2° 2θ, 20.33°±0.2° 2θ, 20.87°±0.2° 2θ, 21.49°±0.2° 2θ, 21.71°±0.2° 2θ, 21.97°±0.2° 2θ, 22.59°±0.2° 2θ, 23.01°±0.2° 2θ, 23.50°±0.2° 2θ, 23.80°±0.2° 2θ, 24.66°±0.2° 2θ, 25.39°±0.2° 2θ, and 25.70°±0.2° 2θ.

According to one or more embodiments of the present disclosure, the crystal form of the compound of Formula (I) and fumaric acid was characterized and analyzed by X-ray powder diffractometer PANalytical Empyrean (PANalytical, NL), in which the 2θ scan angle was from 3° to 45°, the scan step was 0.013°, the test time was 5 minutes and 8 seconds, the phototube voltage and current during test were 45 kV and 40 mA, respectively, and the sample pan was zero background sample pan. In particular, the crystal form was irradiated with Cu-Kα radiation, and the characteristic peaks of the X-ray powder diffraction pattern represented by 2θ value±0.2° are shown in the following table.

| XRPD diffraction peak data of crystal form A of compound of Formula (I) and fumaric acid | | |
|---|---|---|
| Diffraction angle 2θ(°) | d value | Relative intensity (%) |
| 5.98 | 14.78 | 6.5 |
| 7.81 | 11.34 | 9.6 |
| 9.50 | 9.33 | 20.5 |
| 10.14 | 8.74 | 11.4 |
| 10.94 | 8.11 | 24.4 |
| 11.50 | 7.73 | 10.5 |
| 11.93 | 7.45 | 9.2 |
| 12.31 | 7.22 | 9.9 |
| 13.35 | 6.67 | 7.4 |
| 13.81 | 6.45 | 14.3 |
| 14.73 | 6.06 | 9.5 |
| 15.13 | 5.90 | 3.0 |
| 15.59 | 5.73 | 2.8 |
| 16.35 | 5.47 | 5.0 |
| 17.09 | 5.24 | 4.9 |
| 17.57 | 5.10 | 3.0 |
| 17.94 | 5.00 | 8.6 |
| 18.07 | 4.96 | 8.0 |
| 18.61 | 4.82 | 20.2 |
| 19.06 | 4.71 | 20.6 |
| 19.49 | 4.61 | 8.4 |
| 19.82 | 4.54 | 5.7 |
| 20.33 | 4.43 | 5.9 |
| 20.87 | 4.32 | 9.8 |
| 21.49 | 4.20 | 9.5 |
| 21.71 | 4.16 | 4.7 |
| 21.97 | 4.11 | 9.3 |
| 22.59 | 4.01 | 13.9 |
| 23.01 | 3.94 | 7.2 |
| 23.50 | 3.86 | 62.2 |
| 23.80 | 3.81 | 19.7 |
| 24.66 | 3.69 | 100.0 |
| 25.39 | 3.59 | 10.3 |
| 25.70 | 3.55 | 7.2 |

According to an embodiment of the present disclosure, a differential scanning calorimetry spectrum of the crystal form of the compound of Formula (I) and fumaric acid has an endothermic peak at 274° C.±2° C. More preferably, the differential scanning calorimetry spectrum is as shown in FIG. 1. Preferably, a thermogravimetric analysis spectrum of the crystal form of the compound of Formula (I) and fumaric acid shows that the crystal form has basically no weight loss or a weight loss less than 0.5% during a process of being heated to 150° C.±2° C., and the crystal form decomposes at 240° C.±2° C. More preferably, the thermogravimetric analysis spectrum is as shown in FIG. 1.

According to an embodiment of the present disclosure, in the crystal form, a molar ratio of the compound of Formula (I) to fumaric acid is about 1:1.

According to an embodiment of the present disclosure, an HPLC purity of the crystal form of the compound of Formula (I) and fumaric acid of the present disclosure is 98% or higher, preferably 98.5% or higher, further preferably 99% or higher, more preferably 99.95% or higher; furthermore, preferably 99.95% or higher, and a maximum content of a single impurity in this crystal form does not exceed 0.1%. Unless otherwise specified, the term "purity" or "impurity content" used herein refers to the purity percentage of the main peak or impurity peak calculated by peak area normalization using the result of the analysis of the test sample by high performance liquid chromatography.

According to an embodiment of the present disclosure, in the crystal form, the compound of Formula (I) and fumaric acid may be present in the form of a co-crystal of the two, or in the form of a salt of the two. In other words, the crystal form may include or may be the co-crystal of the compound of Formula (I) and fumaric acid, or a fumarate salt of the compound of Formula (I).

Active Pharmaceutical Ingredient

In a second aspect of the present disclosure, the present disclosure provides the following embodiments and/or any combination thereof.

In the second aspect of the present disclosure, the present disclosure provides an active pharmaceutical ingredient (API) containing the crystal form described in the first aspect, i.e., the crystal form comprising the compound of Formula I and fumaric acid.

The term "active pharmaceutical ingredient" refers to a raw material drug used for the preparation of various formulations, which is an active ingredient in the formulation(s) and in the form of powder, crystal, etc. prepared by chemical synthesis or biotechnological techniques for medicinal purposes, but a substance that the subject cannot take directly.

According to an embodiment of the present disclosure, the API satisfies at least one of the following conditions: (1) the particle size $D_{90}$ of the API ranges from about 5 μm to about 60 μm; or (2) the particle size $D_{50}$ of the API does not exceed about 30 μm. In a particular embodiment of the present disclosure, the particle size $D_{90}$ of the API ranges from about 5 μm to about 60 μm (e.g., from 10 μm to 40 μm), and the particle size $D_{50}$ of the API is smaller than or equal to about 30 μm (e.g., smaller than or equal to about 20 μm).

According to an embodiment of the present disclosure, the particle size $D_{90}$ of the API is not smaller than about 10 μm.

According to an embodiment of the present disclosure, the particle size $D_{90}$ of the API ranges from about 10 μm to 40 μm.

According to an embodiment of the present disclosure, the particle size $D_{50}$ of the API is not smaller than about 5 μm.

According to an embodiment of the present disclosure, the particle size $D_{50}$ of the API is smaller than or equal to about 20 μm.

The inventors found through creative research that the API of the present disclosure within the specific particle size (e.g., $D_{50}$ and/or $D_{90}$) range can enable the pharmaceutical composition containing the API to have a higher dissolution rate and a higher dissolution. Moreover, when the pharmaceutical composition of the present disclosure is in the form of tablets, in which the excipients are same, the API of the present disclosure within the specific particle size (such as $D_{50}$ and/or $D_{90}$) range can allows the tablets to have acceptable friability, and no significant sticking or picking phenomenon during tablet preparation (e.g., tableting).

Pharmaceutical Composition

In a third aspect of the present disclosure, the present disclosure provides the following embodiments and/or any combination thereof.

In the third aspect of the present disclosure, the present disclosure provides a pharmaceutical composition comprising: an active ingredient, the active ingredient being the crystal form of the first aspect (i.e., the crystal form A of the compound of Formula (I) and fumaric acid) or a mixture of the crystal form and an amorphous form of the compound of Formula (I) and fumaric acid, or the active pharmaceutical ingredient (API) of the second aspect; and physiologically or pharmaceutically acceptable excipient(s).

According to an embodiment of the present disclosure, the pharmaceutical composition consists of the active ingredient (e.g., the crystal form of the first aspect or the API of the second aspect) and the physiologically or pharmaceutically acceptable excipient.

According to an embodiment of the present disclosure, the physiologically or pharmaceutically acceptable excipient(s) includes one or more selected from the group consisting of filler(s), disintegrant(s), lubricant(s), binder(s), and glidant(s).

The pharmaceutical composition of the present disclosure is preferably a solid preparation.

The pharmaceutical composition of the present disclosure may be formulated in a form suitable for oral, inhalation, topical, nasal, rectal, transdermal, or injection administration.

The pharmaceutical composition of the present disclosure can be administered orally.

The pharmaceutical composition of the present disclosure is preferably prepared into a dosage form of an oral preparation. The shape of the oral preparation is not particularly limited, and may be any of a circle, a small capsule, a doughnut, a rectangle, and the like.

For solid preparations, for example, tablets, capsules, powders, granules, lozenges and the like may be involved.

Solid preparations may be coated with a coating agent, and may have labels and letters for identification and score lines for splitting. Coating is carried out with the addition of conventional coating media and film-forming agents (often collectively referred to as coating materials) familiar to those skilled in the art. The coating can be performed using, for example, a sugar coating base, a water-soluble film coating base, an enteric film coating base, a sustained release film coating base, and the like. For the sugar coating base, a combination of sucrose and one or more substances selected from the group consisting of talc, precipitated calcium carbonate, gelatin, acacia, amylopectin, carnauba wax, and the like can be used. For the water-soluble film coating base, for example, the following can be used: cellulose polymers such as hydroxypropyl cellulose, hydroxypropyl methyl cellulose, hydroxyethyl cellulose, methyl hydroxyethyl cellulose, etc.; synthetic polymers, such as polyvinyl acetal diethylaminoacetate, aminoalkyl methacrylate copolymer E [Eudragit E (trade name)], polyvinylpyrrolidone, etc.; polysaccharides, such as amylopectin, etc. For the enteric film coating base, for example, the following can be used: cellulose polymers, such as hydroxypropyl methylcellulose phthalate, hydroxypropyl methylcellulose acetate succinate, carboxymethyl ethyl cellulose, cellulose acetate phthalate, etc.; acrylic polymers, such as methacrylic acid copolymer L [Eudragit L (trade name)], methacrylic acid copolymer LD [Eudragit L-30 D55 (trade name)], methacrylic acid copolymer S [Eudragit S (trade name)], etc.; and naturally occurring substances, such as shellac, etc.; etc. For the sustained-release film coating base, for example, the following can be used: cellulose polymers, such as ethyl cellulose, cellulose acetate, etc.; acrylic polymers such as aminoalkyl methacrylate copolymer RS [Eudragit RS (trade name)], ethyl acrylate-methyl methacrylate copolymer suspension [Eudragit NE (trade name)], etc. Two or more of the above-mentioned coating bases may be mixed and used in a suitable ratio. Furthermore, coating additives can also be used in the coating. For coating additives, for example, the following can be used: light-masking agents and/or colorants, such as titanium oxide, talc, iron oxide, etc.; plasticizers, such as polyethylene glycol, triethyl citrate, castor oil, polysorbate, etc.; organic acids, such as citric acid, tartaric acid, malic acid, ascorbic acid, etc.

Solid preparations can be formulated for immediate release and/or modified release. The examples of modified release include delayed release, sustained release, pulsed release, controlled release, targeted release, and programmed release.

When the solid preparation is a tablet, any pharmaceutically acceptable excipient generally used for the production of solid preparations can be used. Tablets may be prepared by compression or molding, optionally with one or more physiologically or pharmaceutically acceptable excipients. Compressed tablets may also be prepared by compressing in a suitable machine the active ingredient in a free-flowing form (such as powder or capsule), which is optionally mixed with a binder, lubricant, filler, solubilizer, or disintegrant. Molded tablets may be prepared by molding in a suitable machine a mixture of the moistened and powdered compound with an inert liquid dispersion medium. Tablets may optionally be coated or scored, and may be formulated to provide sustained or controlled release of the active ingredient therein. Tablet formulation is discussed in detail in "Pharmaceutical Dosage Forms: Tablets, Vol. 1", by H. Lieberman and L. Lachman, Marcel Dekker, N.Y., 1980.

When the solid preparation is a capsule, any conventional encapsulation is suitable, for example using the above-mentioned carriers in a hard gelatin capsule. When the composition is in the form of a soft gelatin capsule, any physiologically or pharmaceutically acceptable excipient commonly used in the preparation of dispersions or suspensions may be considered, and the physiologically or pharmaceutically acceptable excipient is incorporated into the soft gelatin capsule.

The pharmaceutical preparation can be conveniently presented in the form of a unit dose and can be prepared by any of the methods well known in the art of pharmacy, so that a unit dose can be administered to a subject. Preferably, the pharmaceutical composition is in the form of a unit dose, e.g., a solid preparation (e.g., tablet, powder, dry suspension, granule, or capsule) in the form of a unit dose.

The term "starch" generally denotes a substance having the empirical formula $(C_6H_{10}O_5)_n$ (where n is in the range from 300 to 1000) and a molecular weight of 50,000 to 160,000 and consisting of amylose and amylopectin, both of which are polysaccharides based on α-glucose units. Starch is derived from plant materials and typically exists in the form of very tiny particles (5 μm to 25 μm in diameter) composed of stratified layers of starch molecules that are formed around the nucleus. Starch particles can be round, oval or angular and consist of radio-oriented crystalline aggregates of two anhydrous D-glucose polymers (amylose and amylopectin). Amylose is a linear polymer of hundreds of glucose units linked by alpha-1,4 glycosidic bonds. Amylopectin is a branched polymer of thousands of glucose units with alpha-1,6 glycosidic bonds at branch sites and alpha-1,4 bonds in linear regions. Certain branches can have 20 to 30 glucose residues. Specifically, the starch is selected from starches having an amylose content ranging from 10% to 40% by weight. Typical examples are corn starch, potato starch, rice starch, tapioca starch, and wheat starch.

The term "pregelatinized starch" is intended to define starch that has been chemically and/or mechanically processed to break up all or part of the particles in the presence of water and subsequently dried. Some types of pregelatinized starches can be modified to have improved compressibility and flowability characteristics. A typical pregelatinized starch contains 5% free amylose, 15% free amylopectin, and 80% unmodified starch. The pregelatinized starch can be corn starch processed chemically and/or mechanically as described above. Other types of starch than corn starch can be pregelatinized, such as rice or potato starch.

According to an embodiment of the present disclosure, based on a total weight of the pharmaceutical composition, the pharmaceutical composition comprises 15% to 60% (e.g., 25% to 45%) by weight or 2% to 45% (e.g., 5% to 29% or 30% to 44%) by weight of the active ingredient. Specifically, a weight percentage of the active ingredient in the pharmaceutical composition may be 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 40.64%, 41%, 42%, 43%, 44%, 45%, 46%, 47%, 48%, 49%, 50%, 51%, 52%, 53%, 54%, 55%, 56%, 57%, 58%, 59%, or 60%.

According to an embodiment of the present disclosure, the physiologically or pharmaceutically acceptable excipient(s) includes one or more selected from the group consisting of filler(s), disintegrant(s), lubricant(s), binder(s), and glidant(s). Specifically, the physiologically or pharmaceutically acceptable excipient(s) is one or more selected from the group consisting of filler(s), disintegrant(s), lubricant(s), binder(s), and glidant(s). More specifically, the physiologically or pharmaceutically acceptable excipient(s) consists of filler(s), disintegrant(s), lubricant(s), binder(s), and glidant(s).

According to an embodiment of the present disclosure, a weight ratio of the active ingredient to the filler(s) is in the range from 1:5 to 1:1 (e.g., in the range from 1:2 to 1:1) or from 1:3 to 3:1 (e.g., in the range from 1:2 to 2:1, specifically in the range from 1:1 to 1:1.5).

According to an embodiment of the present disclosure, a weight ratio of the disintegrant(s) to the lubricant(s) is in the range from 1:4 to 4:1, specifically in the range from 1:2 to 2:1, more specifically in the range from 1:1 to 2:1, for example, in the range from 1:0.8 to 1:0.7.

According to an embodiment of the present disclosure, a weight ratio of the glidant(s) to the lubricant(s) is in the range from 1:3 to 3:1 (e.g., in the range from 1:2 to 2:1, specifically in the range from 1:1 to 2:1, more specifically in the range from 1:1 to 1.5:1, e.g., in the range from 1:0.8 to 1:0.7.

According to an embodiment of the present disclosure, a weight ratio of the binder(s) to the lubricant(s) is in the range from 1:3 to 3:1, specifically in the range from 1:2 to 2:1, for example 1:1.

According to an embodiment of the present disclosure, a weight percentage of the filler(s) in the pharmaceutical composition is in the range from 10% to 80%, further from 30% to 70%, preferably from 30% to 65% or from 40% to 60%, for example 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, or 80%.

Alternatively, a content of the filler(s) in the pharmaceutical composition (e.g., the pharmaceutical composition in the form of a unit dose) is in the range from 110 mg to 265 mg, preferably from 130 mg to 245 mg, for example, 110 mg, 120 mg, 130 mg, 140 mg, 150 mg, 160 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 260 mg, or 265 mg.

According to an embodiment of the present disclosure, the filler(s) includes one or more selected from the group consisting of lactose, anhydrous calcium bicarbonate, sugar alcohol(s), cellulose, or starch. For example, the sugar alcohol(s) as the filler(s) includes one or more selected from the group consisting of mannitol, maltitol, erythritol, lactitol, sorbitol, and xylitol. For example, the cellulose as the filler(s) includes one or more selected from the group consisting of microcrystalline cellulose, powdered cellulose, and silicified microcrystalline cellulose. For example, the starch as the filler(s) includes one or more of corn starch, potato starch, sweet potato starch, and pregelatinized starch; preferably, it is pregelatinized starch.

Specifically, the filler(s) is one or more selected from the group consisting of lactose, anhydrous calcium bicarbonate, sugar alcohol, cellulose, and starch. For example, the sugar alcohol as the filler(s) is one or more selected from the group consisting of mannitol, maltitol, erythritol, lactitol, sorbitol, and xylitol; preferably, it is mannitol. For example, the cellulose as the filler(s) is one or more selected from the group consisting of microcrystalline cellulose, powdered cellulose, and silicified microcrystalline cellulose; preferably, it is microcrystalline cellulose and/or silicified microcrystalline cellulose. For example, the starch as the filler(s) is one or more selected from the group consisting of corn starch, potato starch, sweet potato starch, and pregelatinized starch; preferably, it is pregelatinized starch.

According to an embodiment of the present disclosure, the filler(s) is microcrystalline cellulose, pregelatinized starch, lactose, mannitol (such as D-mannitol), or a mixture of two or more thereof (for example, a mixture of microcrystalline cellulose and pregelatinized starch, or a mixture of microcrystalline cellulose and mannitol (such as D-mannitol)). When the filler(s) is a mixture of microcrystalline cellulose and pregelatinized starch, a weight ratio of the two is in a range from 1.5:1 to 3.5:1, for example 1.9:1, 2:1, 2.1:1, 2.3:1, 2.4:1, 2.5:1, 2.8:1, 2.9:1, 3:1, or 3.1:1; when the filler(s) is a mixture of microcrystalline cellulose and mannitol (such as D-mannitol), a weight ratio of the two is in a range from 1:5 to 5:1, for example from 1:3.5 to 3.5:1, for example 3.1:1 or 3.2:1. In the pharmaceutical composition of the present disclosure, if the weight ratio of the two fillers (for example, in the mixture of microcrystalline cellulose and pregelatinized starch, or in the mixture of microcrystalline cellulose and mannitol (such as D-mannitol)) described above is lower than or higher than the above-mentioned range, there is capping phenomenon during the process of preparation (such as tableting) of the pharmaceutical composition, which does not meet the pharmaceutical requirements.

According to an embodiment of the present disclosure, a weight percentage of the disintegrant(s) in the pharmaceutical composition ranges from 1% to 10%, specifically from 1% to 5%, for example 2%, 3%, or 4%. In the pharmaceutical composition of the present disclosure, the amount of the disintegrant(s) should not be too low or too high. If the amount of the disintegrant(s) is too low (for example, its weight percentage in the pharmaceutical composition is less than 1%), the dissolution rate of the active ingredient will be too low, the dissolution within 60 min (if it still does not reach 60%) cannot meet the pharmaceutical requirements; if the amount is too high (for example, its weight percentage in the pharmaceutical composition exceeds 5%), the dissolution rate of the active ingredient will be too high, almost all active ingredient disintegrated and dissolved in a short time (such as a period of from 5 min to 10 min) (the dissolution is greater than 80% or even 90%), which does not meet the pharmaceutical requirements.

Alternatively, a content of the disintegrant(s) in the pharmaceutical composition (e.g., the pharmaceutical composition in the form of a unit dose) may be in a range from 3.5 mg to 19 mg, such as 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, or 19 mg.

According to an embodiment of the present disclosure, the disintegrant(s) includes one or more selected from the group consisting of crospovidone, croscarmellose sodium, low-substituted hydroxypropyl cellulose, carboxymethyl starch sodium, corn starch, and potato starch. Specifically, the disintegrant(s) is one or more selected from the group consisting of crospovidone, croscarmellose sodium, low-substituted hydroxypropyl cellulose, carboxymethyl starch sodium, corn starch, and potato starch. Preferably, the disintegrant(s) is one or more selected from the group consisting of crospovidone, croscarmellose sodium, and carboxymethyl starch sodium.

According to an embodiment of the present disclosure, a weight percentage of the lubricant(s) in the pharmaceutical composition is in a range from 0.5% to 5%, further from 0.5% to 4%, particularly from 0.5% to 3%, more particularly from 1% to 2%, for example 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 4% or 5%. In the pharmaceutical composition of the present disclosure, the amount of the lubricant(s) should not be too low or too high. If the amount of the lubricant is too low or too high (for example, its weight percentage in the pharmaceutical composition is less than 0.5% or more than 4%), the phenomenon of powder adhesion, sticking, or picking will occur during the preparation (such as tableting) of the pharmaceutical composition, which does not meet the pharmaceutical requirements.

Alternatively, a content of the lubricant(s) in the pharmaceutical composition (e.g., the pharmaceutical composition in the form of a unit dose) may be in a range from 1.5 mg to 15 mg, for example, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 13 mg, or 14 mg.

According to an embodiment of the present disclosure, the lubricant(s) includes one or more selected from the group consisting of magnesium stearate, calcium stearate, zinc stearate, hydrogenated vegetable oil, glyceryl behenate, stearic acid, and sodium stearyl fumarate. Specifically, the lubricant(s) is one or more selected from the group consisting of magnesium stearate, calcium stearate, zinc stearate, hydrogenated vegetable oil, glyceryl behenate, stearic acid, and sodium stearyl fumarate; preferably, the lubricant(s) is one or more selected from the group consisting of magnesium stearate, glyceryl behenate, and sodium stearyl fumarate. Preferably, the lubricant(s) is magnesium stearate, or a combination of magnesium stearate and sodium stearyl fumarate.

According to an embodiment of the present disclosure, a weight percentage of the glidant(s) in the pharmaceutical composition is in a range from 0.5% to 5%, further from 0.5% to 4%, particularly from 0.5% to 3%, more particularly from 2% to 3%, for example, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, or 4%. In the pharmaceutical composition of the present disclosure, the amount of the glidant(s) should not be too low or too high. If the amount used is too low or too high (for example, its weight percentage in the pharmaceutical composition is less than 0.5% or more than 4%), the phenomenon that the tablet weight of the obtained tablets is unstable may occur during the preparation of tablets of the pharmaceutical composition, which does not meet the pharmaceutical requirements.

Alternatively, a content of the glidant(s) in the pharmaceutical composition (e.g., the pharmaceutical composition in the form of a unit dose) may be in a range from 1.5 mg to 15 mg, for example, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 13 mg, or 14 mg.

According to an embodiment of the present disclosure, the glidant(s) includes colloidal silica and/or talc. Specifically, the glidant(s) is selected from colloidal silica and/or talc; for example, the glidant(s) is colloidal silica.

The term "colloidal silica" as used herein is also referred to as "light anhydrous silicic acid".

According to an embodiment of the present disclosure, a weight percentage of the binder(s) in the pharmaceutical composition is in a range from 0 to 10%, further from 1% to 5%, particularly from 1% to 3%, for example 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.5%, 4%, 4.5%, or 5%. In the pharmaceutical composition of the present disclosure, the amount of the binder(s) should not be too low or too high. If the amount of the binder(s) is too low or too high (for example, its weight percentage in the pharmaceutical composition is less than 1% or more than 5%), the phenomenon that the hardness of the obtained tablet is too low (e.g., lower than 40N) or too high (e.g., higher than 80N) may occur during the preparation of the tablets of the pharmaceutical composition, which does not meet the pharmaceutical requirements.

Alternatively, a content of the binder(s) in the pharmaceutical composition (e.g., the pharmaceutical composition in the form of a unit dose) may be in a range from 1 mg to 15 mg, more preferably from 5 mg to 8 mg, for example, 1 mg, 2 mg, 3 mg, 4 mg, 5 mg, 5.5 mg, 6 mg, 6.5 mg, 7 mg, 7.5 mg, 8 mg, 9 mg, 10 mg, 11 mg, 12 mg, 13 mg, or 14 mg.

Specifically, the binder(s) is one or more selected from the group consisting of hypromellose, hydroxypropyl cellulose, methyl cellulose, hydroxyethyl cellulose, carboxymethyl cellulose, copovidone, and polyvinylpyrrolidone; preferably, it is hypromellose, hydroxypropyl cellulose, and/or copovidone.

According to an embodiment of the present disclosure, the physiologically or pharmaceutically acceptable excipient further includes suspending agent(s) and/or flavoring agent(s).

Specifically, the suspending agent(s) is selected from the group consisting of low-molecular-weight suspending agent(s), high-molecular-weight suspending agent(s), silicate(s), thixotrope(s), and any combination thereof. Specifically, the low-molecular-weight suspending agent(s) can be selected from the group consisting of glycerin, syrup, and any combination thereof; the high-molecular-weight suspending agent(s) can be selected from the group consisting of tree gums (such as acacia, tragacanth, peach gum, or any combination thereof), plant mucilage and polysaccharides (such as sodium alginate, agar, starch, pectin, carrageenan, chitosan, or any combination thereof), cellulose derivatives (such as methylcellulose or salts thereof, carboxymethylcellulose or salts thereof, hydroxypropyl cellulose or salts thereof, hydroxyethyl cellulose or salts thereof, or any combination thereof), and any combination thereof; the silicate can be selected from the group consisting of bentonite, magnesium aluminum silicate, aluminum silicate, and any combination thereof; and/or, the thixotrope can be selected from the group consisting of citrate, hydrogen citrate, tartrate, hydrogen tartrate, phosphate, $AlCl_3$, and any combination thereof. Preferably, the suspending agent(s) is one or more selected from the group consisting of hypromellose, hydroxypropyl cellulose, methyl cellulose, sodium carboxymethyl cellulose, sucrose, glycerin, sorbitol, maltitol, xanthan gum, tragacanth, polyacrylic acid cross-linked polymer, polyvinylpyrrolidone, and microcrystalline cellulose.

Specifically, a weight percentage of the suspending agent(s) in the pharmaceutical composition is in a range from 0 to 30%, preferably from 1% to 20%.

Specifically, the flavoring agent(s) is selected from ascorbic acid, aspartic acid, aspartame, sucralose, saccharin, D-sorbitol, stevia, acesulfame potassium, thamatin, advantame, glycine, sodium chloride, magnesium chloride, hydrochloric acid, dilute hydrochloric acid, citric acid and salts thereof, anhydrous citric acid, L-glutamic acid and salts thereof, succinic acid and salts thereof, acetic acid, tartaric acid and salts thereof, sodium bicarbonate, fumaric acid and salts thereof, malic acid and salts thereof, glacial acetic acid, disodium inosinate, honey, reduced maltose syrup (maltitol), licorice, xylitol, etc.; and ascorbic acid is preferred.

Specifically, a weight percentage of the flavoring agent(s) in the pharmaceutical composition is in a range from 0.01% to 10%, preferably from 0.05% to 7.5%, more preferably from 1% to 5%.

In a specific embodiment, the filler(s) is a mixture of microcrystalline cellulose and D-mannitol (for example, a weight ratio of the two is as defined in this disclosure); the binder(s) is hydroxypropyl cellulose; the disintegrant(s) is croscarmellose sodium; the glidant(s) is colloidal silica; and/or, the lubricant(s) is magnesium stearate. Particularly, the weight percentages or contents of the above specific physiologically or pharmaceutical acceptable excipients (such as microcrystalline cellulose, D-mannitol, croscarmellose sodium, hydroxypropyl cellulose, colloidal silica and/or magnesium stearate) are as defined above.

In a specific embodiment, the filler(s) is a mixture of microcrystalline cellulose and pregelatinized starch (for example, a weight ratio of the two is as defined in the present disclosure); the binder(s) is hydroxypropyl cellulose; the disintegrant(s) is croscarmellose sodium; the glidant(s) is colloidal silica; and/or the lubricant(s) is magnesium stearate. Particularly, the weight percentages or the weight ratios of the above specific physiologically or pharmaceutical acceptable excipients (such as microcrystalline cellulose, pregelatinized starch, croscarmellose sodium, hydroxypropyl cellulose, colloidal silica and/or magnesium stearate) in the pharmaceutical composition are as defined above.

According to an embodiment of the present disclosure, the pharmaceutical composition is an oral preparation, preferably an oral solid preparation (e.g., tablet, powder, dry suspension, granule, or capsule).

In the embodiment of the present disclosure, the pharmaceutical composition is in the form of a unit dose, such as a solid preparation in the form of a unit dose (e.g., tablet, powder, dry suspension, granule, or capsule).

Preferably, when the oral solid preparation of the present disclosure is a tablet, the tablet may have a film coating for an easy-to-swallow tablet, or the tablet has no film coating.

The "hardness" of a tablet is measured in N (Newtons) as the force required to break the tablet. According to an embodiment of the present disclosure, the tablet of the present disclosure has a hardness in the range from 30N to 90N, for example, in the range from 40N to 80N, or for example, 70N. It is well known to those skilled in the art to define a suitable hardness range depending on the size and shape of the tablet.

According to an embodiment of the present disclosure, when the pharmaceutical composition of the present disclosure is in the form of a unit dose (e.g., solid preparations, such as tablet, powder, dry suspension, granule, or capsule, in the form of a unit dose), the pharmaceutical composition comprises 1 mg to 500 mg, preferably 10 mg to 300 mg, more preferably 50 mg to 200 mg, most preferably 120 mg to 155 mg, for example, 1 mg, 2 mg, 3 mg, 4 mg, 5 mg, 6 mg, 7 mg, 8 mg, 9 mg, 10 mg, 20 mg, 30 mg, 40 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 151 mg, 152 mg, 200 mg, or 250 mg of the active ingredient (e.g., the crystal form of the first aspect or the API of the second aspect) per unit dose. Alternatively, when the pharmaceutical composition of the present disclosure is in the form of a unit dose (e.g., solid preparations, such as tablet, powder, dry suspension, granule, or capsule, in the form of a unit dose), the pharmaceutical composition includes 40 mg to 170 mg, preferably 95 mg to 130 mg of a free base of the active ingredient per unit dose. For example, the pharmaceutical composition includes 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 62.1 mg, 62.2 mg, 62.3 mg, 62.4 mg, 62.5 mg, 62.6 mg, 62.7 mg, 62.8 mg, 62.9 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 135 mg, 140 mg, 145 mg, 150 mg, 155 mg, 160 mg, 165 mg, or 170 mg of the free base of the active ingredient per unit dose.

When the pharmaceutical composition of the present disclosure is an oral preparation (such as tablet, powder, dry suspension, granule, capsule), it is convenient for administration to subject(s), or improves compliance of using drug for subject(s) (especially children, the elderly, or patients with dysphagia) and avoids the risk of overdose of injectable drugs.

The inventors had also investigated preparation parameters such as in vitro dissolution of the pharmaceutical composition (e.g., tablet) comprising the crystal form A of the compound of Formula (I) and fumaric acid. The results showed that in the same dissolution medium, the pharmaceutical composition (specifically, tablet) comprising the crystal form A had a higher dissolution rate and a higher in vitro dissolution, which can meet the dissolution requirements.

According to an embodiment of the present disclosure, the subject is human being, preferably a child, an adult, or an elderly person, such as a child aged 0 to 18 years (e.g., 0 to 12 years old), an adult aged 19 to 59 years or an elderly person aged 60 years or older. Specifically, when the pharmaceutical composition of the present disclosure is a granule or dry suspension, the subject is preferably a child (such as a child aged 0 to 12 years); when the pharmaceutical composition of the present disclosure is a tablet or capsule, the subject is preferably an adult or an elderly person, for example, adults aged 19 to 59 years or elderly persons aged 60 or older; when the pharmaceutical composition of the present disclosure is an oral liquid preparation, the subject is preferably a child (such as a child aged 0 to 12 years), an elderly person (an elderly person aged 60 years or older), or a patient with dysphagia.

After the pharmaceutical composition of the present disclosure is placed under the conditions of accelerated stability test (such as 40° C.±2° C. and 75%±5% RH) for 1 month or 3 months, the maximum content of a single impurity is not more than 0.2% (such as not more than 0.1%) and/or a total impurity content is not more than 1% (such as no more than 0.25%).

In addition, the pharmaceutical composition of the present disclosure has a high dissolution, a high dissolution rate and/or high stability. Moreover, the pharmaceutical composition of the present disclosure is suitable for formulation into oral preparations, especially oral solid preparations such as tablets (with good tablet compressibility), and suitable for large-scale industrial production, and the quality of the obtained products is stable and reliable, with good clinical application value.

According to an embodiment of the present disclosure, the pharmaceutical composition of the present disclosure is a tablet, in which the active ingredient (the active pharmaceutical ingredient described in the second aspect) is within a specific particle size ($D_{50 \leq 30}$ μm and/or $D_{90}$ in the range from 5 μm to 60 μm) range; the filler(s) is a mixture of microcrystalline cellulose and D-mannitol (for example, a weight ratio of the two is as defined in the present disclosure) or a mixture of microcrystalline cellulose and pregelatinized starch (for example, a weight ratio of the two is as defined in the present disclosure); the binder(s) is hydroxypropyl cellulose; the disintegrant(s) is croscarmellose sodium; the glidant(s) is colloidal silica; and/or the lubricant(s) is magnesium stearate. Particularly, the weight percentages or contents of the above specific physiologically or pharmaceutical acceptable excipients (such as microcrystalline cellulose, mannitol, croscarmellose sodium, hydroxypropyl cellulose, colloidal silica and/or magnesium stearate) are as defined above. The pharmaceutical composition has a high dissolution rate, a high dissolution, and acceptable fragility, and there is no significant sticking or picking phenomenon during the tablet preparation process (such as tableting process).

Others

In the fourth aspect of the present disclosure, the present disclosure provides the following embodiments and/or any combination thereof.

In the fourth aspect of the present disclosure, the present disclosure provides a method for treating a disease caused by a coronavirus, including: administering the pharmaceutical composition of the third aspect of the present disclosure to a subject.

According to an embodiment of the present disclosure, the coronavirus is 2019-nCoV.

According to an embodiment of the present disclosure, the subject is human being, preferably a child, an adult, or an elderly person, such as a child aged 0 to 18 years (e.g., 0 to 12 years old), an adult aged 19 to 59 years, or an elderly person aged 60 years or older. Specifically, when the pharmaceutical composition of the present disclosure is a granule or dry suspension, the subject is preferably a child (such as a child aged 0 to 12 years); when the pharmaceutical composition of the present disclosure is a tablet or capsule, the subject is preferably an adult or an elderly person, for example, adults aged 19 to 59 years or elderly persons aged 60 or older; when the pharmaceutical composition of the present disclosure is an oral liquid preparation, the subject is preferably a child (such as a child aged 0 to 12 years), an elderly person (such as an elderly person aged 60 years or older), or a patient with dysphagia.

In a fifth aspect of the present disclosure, the present disclosure provides the following embodiments and any combination thereof.

In the fifth aspect of the present disclosure, the present disclosure also provides a production method of the pharmaceutical composition, including: premixing, granulation, and/or mixing; preferably, the method includes the following steps: (i) premixing: mixing the active ingredient with the physiologically or pharmaceutically acceptable excipient(s) (such as one or more physiologically or pharmaceutically acceptable excipient(s) described above, for example, one filler described above); (ii) granulation: granulating the mixture obtained in step (i) (such as dry granulation or wet granulation), followed by sieving; and (iii) mixing: mixing particles obtained in step (ii) with one or more other physiologically or pharmaceutically acceptable excipients except the physiologically or pharmaceutically acceptable excipient(s) described in step (i).

According to an embodiment of the present disclosure, in the production method of the pharmaceutical composition of the present disclosure, step (i) is achieved by the following operations: mixing the active ingredient (for example, the crystal form of the first aspect or the API of the second aspect) with the filler(s), the disintegrant(s), an optional binder, an optional solubilizer, and the glidant(s) in sequence. Specifically, step (i) is achieved by the following operations: firstly, mixing the active ingredient and the filler(s), and then adding the disintegrant(s), the optional binder(s), the optional solubilizer(s), and the glidant(s) for mixing. Preferably, step (i) is achieved by the following operations: firstly mixing the active ingredient and a first filler, then adding a second filler, the disintegrant(s), the optional binder(s), the optional solubilizer(s), and the glidant(s) for mixing. Particularly, the first filler and the second filler may be the same or different; preferably, the first filler is the cellulose as the filler(s) of the present disclosure, and the second filler is the starch as the filler(s) of the present disclosure. Preferably, the mixing is achieved by stirring, preferably by hand stirring or by stirring in a mixing device such as a hopper mixer.

According to an embodiment of the present disclosure, in the production method of the pharmaceutical composition of the present disclosure, step (ii) is achieved by the following operations: performing wet granulation or dry granulation on the mixture obtained in step (i), and then performing sieving. Specifically, the wet granulation or dry granulation can be performed by those skilled in the art according to formulation requirements. Preferably, the wet granulation is to mix the mixture obtained in step (i) with water, and perform granulation by a wet granulator. Preferably, the dry granulation is to granulate the mixture obtained in step (i) through a dry granulator. Preferably, the sieving is achieved through a 20 to 80-mesh sieve (e.g., a 40 to 60-mesh sieve).

According to an embodiment of the present disclosure, in the production method of the pharmaceutical composition of the present disclosure, step (iii) is achieved by the following operation: mixing the particles obtained in step (ii) with the lubricant(s). Preferably, the mixing is achieved by stirring, preferably by hand stirring or by stirring in a mixing device such as a hopper mixer.

According to an embodiment of the present disclosure, the production method of the pharmaceutical composition of the present disclosure further includes the following step: (iv) tableting the mixture obtained in step (iii).

Specifically, in the pharmaceutical composition, the active ingredient, the physiologically or pharmaceutically acceptable excipient(s), and respective amounts thereof are as defined in the present disclosure.

Specifically, in the production method of the pharmaceutical composition of the present disclosure, step (i) as the premixing step is realized by the following operation: mixing the active ingredient with the filler(s), the disintegrant(s), the binder(s), and the glidant(s) in sequence (uniformly). More specifically, step (i) as the premixing step is realized by the following operations: firstly mixing the active ingredient with a first filler (uniformly), and then adding a second filler, the disintegrant(s), the binder(s), and the glidant(s) for mixing (uniformly). Particularly, the first filler and the second filler may be the same or different. Preferably, when the first filler is the cellulose (such as microcrystalline cellulose) as the filler(s) of the present disclosure, the second filler is the starch (such as pregelatinized starch) as the filler(s) of the present disclosure. Alternatively, when the first filler is the sugar alcohol (such as D-mannitol) as the filler(s) of the present disclosure, the second filler is the cellulose (such as microcrystalline cellulose) as the filler(s) of the present disclosure. Alternatively, when the first filler is the cellulose (such as microcrystalline cellulose) as the filler(s) of the present disclosure, the second filler is the sugar alcohol (such as D-mannitol) as the filler(s) of the present disclosure. Alternatively, when the first filler is the starch (such as pregelatinized starch) as the filler(s) of the present disclosure, the second filler is the cellulose (such as microcrystalline cellulose) as the filler(s) of the present disclosure. Preferably, the mixing is achieved by stirring, preferably by hand stirring or by stirring in a mixing device such as a hopper mixer.

Specifically, step (ii) as the granulation step is achieved by the following operations: performing wet granulation or dry granulation on the mixture obtained in step (i), and then performing sieving. Specifically, the wet granulation or dry granulation can be performed by those skilled in the art according to formulation requirements. Preferably, the wet granulation can be carried out one, two or more times. Preferably, the wet granulation is to mix the mixture obtained in step (i) with a solvent (such as water), followed by granulation through a wet granulator or a fluidized bed, sieving, drying (such as at 40° C. to 80° C.), and optionally secondary sieving. Preferably, the dry granulation is to granulate the mixture obtained in step (i) through a dry granulator, or to compress the mixture obtained in step (i) into large sheets and then smashed and sieved for granulation. Preferably, the sieving or secondary sieving is achieved through a 20 to 80-mesh sieve (e.g., a 40 to 60-mesh sieve). Preferably, the drying is achieved by means of an oven or a fluidized bed.

Specifically, the binder(s) can be added in a manner as follows: 1) in step (i) or (ii), the binder(s) is added in the form of dry powder; 2) in step (ii), the binder(s) is added as a solution (preferably an aqueous solution, for example, an aqueous solution comprising the binder(s) with a concentration of from 2% to 10% by weight); 3) in step (ii), a part of the binder(s) is added in the form of dry powder, and the other part of the binder(s) is added in the form of a solution (preferably an aqueous solution, for example, an aqueous solution comprising the binder(s) with a concentration of from 2% to 15% by weight.

Specifically, the active ingredient is mixed with a part of the binder(s) in a solution (preferably an aqueous solution, such as an aqueous solution comprising the binder(s) with a concentration of from 2% to 10% by weight), followed by granulation, sieving (e.g., 20 to 80-mesh sieve), drying (e.g., drying at a temperature in the range from 40° C. to 80° C.), optional secondary sieving (e.g., 20 to 80-mesh sieve), and then mixing with the first filler, the second filler, the disintegrant(s), the remaining part of the binder(s), and the glidant(s) (uniformly).

Specifically, step (iii) as a mixing step is achieved by mixing the particles obtained in step (ii) with the lubricant(s) (uniformly). Particularly, the mixing is achieved by stirring, preferably by hand stirring or by stirring in a mixing device such as a hopper mixer.

Specifically, the production method further includes a tableting step. Particularly, the tableting step is to tablet the mixture obtained in step (iii); and/or, the tableting step is performed by a tableting machine (e.g., a single punch tableting machine).

The embodiments and technical solutions of different levels described herein can be arbitrarily combined, unless otherwise specified.

The following examples illustrate the present disclosure, but it should not be understood that the scope of the subject matter of the present disclosure is limited to the following examples. All techniques implemented based on the above content of the present disclosure belong to the scope of the present disclosure. The compounds or reagents used in the following examples can be purchased commercially, or prepared by conventional methods known to those skilled in the art; and the experimental instruments used can be purchased commercially. In the present disclosure, the content (%) in the examples refers to the weight percentage of the respective component(s) in the pharmaceutical composition (that is, the tablet obtained in the respective example); the value obtained by dividing the amount (in g) described in the respective example by the batch quantity (i.e., the number of tablets) is the specific content (e.g., in mg or g) of the respective component in the pharmaceutical composition (i.e., the tablet obtained in the respective example).

PRODUCTION AND PATTERN DETERMINATION OF THE CRYSTAL FORM

I. Production of the Crystal Form

Production Example 1

A solid form (15.2 mg) of (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazine-2,4-dione fumaric acid was added to 1.0 mL of acetone to form a suspension, the suspension was stirred at room temperature for 7 days and then separated to obtain a solid. The obtained solid was vacuum-dried to give the crystal form A as a white solid.

Production Example 2

A solid form (15.2 mg) of (6E)-6-[(6-chloro-2-methyl-2H-indazol-5-yl]imino]-3-[(1-methyl-1H-1,2,4-triazol-3-yl)methyl]-1-(2,4,5-trifluorobenzyl)-1,3,5-triazine-2,4-dione fumaric acid was added to 1.0 mL of tetrahydrofuran to form a suspension, the suspension was stirred at room temperature for 7 days and then separated to obtain a solid. The obtained solid was vacuum-dried to obtain the crystal form A as a white solid.

II. Pattern Determination and Data of the Crystal Form

1. XRPD Pattern Determination Conditions and Diffraction Peak Data

Samples of the crystal form A were analyzed with an X-ray powder diffractometer PANalytical Empyrean (PANalytical, NL). The 2θ scan angle was from 3° to 45°, the scan step was 0.013°, and the test time was 5 minutes and 8 seconds. The phototube voltage and current for testing the samples were 45 kV and 40 mA, respectively, and the sample pan was a zero background sample pan.

| XRPD diffraction peak data of crystal form A of compound of Formula (I) and fumaric acid | | |
|---|---|---|
| Diffraction angle 2θ(°) | d value | Relative intensity (%) |
| 5.98 | 14.78626 | 6.5 |
| 7.81 | 11.34346 | 9.6 |
| 9.50 | 9.33476 | 20.5 |
| 10.14 | 8.74826 | 11.4 |
| 10.94 | 8.11497 | 24.4 |
| 11.50 | 7.73053 | 10.5 |
| 11.93 | 7.45358 | 9.2 |
| 12.31 | 7.22640 | 9.9 |
| 13.35 | 6.67381 | 7.4 |
| 13.81 | 6.45577 | 14.3 |
| 14.73 | 6.06092 | 9.5 |
| 15.13 | 5.90154 | 3.0 |
| 15.59 | 5.73173 | 2.8 |
| 16.35 | 5.47160 | 5.0 |
| 17.09 | 5.24274 | 4.9 |
| 17.57 | 5.10221 | 3.0 |
| 17.94 | 5.00099 | 8.6 |
| 18.07 | 4.96586 | 8.0 |
| 18.61 | 4.82710 | 20.2 |
| 19.06 | 4.71808 | 20.6 |
| 19.49 | 4.61714 | 8.4 |
| 19.82 | 4.54367 | 5.7 |
| 20.33 | 4.43390 | 5.9 |
| 20.87 | 4.32444 | 9.8 |
| 21.49 | 4.20587 | 9.5 |
| 21.71 | 4.16468 | 4.7 |
| 21.97 | 4.11733 | 9.3 |
| 22.59 | 4.01051 | 13.9 |
| 23.01 | 3.94115 | 7.2 |
| 23.50 | 3.86414 | 62.2 |
| 23.80 | 3.81790 | 19.7 |
| 24.66 | 3.69172 | 100.0 |
| 25.39 | 3.59338 | 10.3 |
| 25.70 | 3.55226 | 7.2 |

It can be seen from the above XRPD diffraction peak data that the main characteristic diffraction peaks of the crystal form A include any three characteristic diffraction peaks selected from the group consisting of 10.94, 19.06, 23.50, and 24.66, may further include any one or more characteristic diffraction peaks selected from the group consisting of 9.5, 13.81, 18.61, 22.59, and 23.8, and may further include any one or more characteristic diffraction peaks selected from the group consisting of 7.81, 10.14, 11.50, 11.93, and 12.31, or may further include any one or more characteristic diffraction peaks selected from the group consisting of 14.73, 20.87, 21.49, 21.97, and 25.39, or the main characteristic diffraction peaks of the crystal form A are at 10.94, 19.06, 23.50, 24.66, 9.5, 13.81, 18.61, 22.59, and 23.8.

2. Differential Scanning Calorimetry (DSC) Spectrum Determination Conditions and Data The DSC spectrum of the crystal form A of the compound of Formula (I) and fumaric acid was obtained in the following manner:

A differential scanning calorimeter TA Discovery 2500 (TA, US) was used. 1 mg to 2 mg of the sample was accurately weighed and placed in a perforated DSC Tzero sample pan and heated to the final temperature at a rate of 10° C./min with a nitrogen purge rate of 50 mL/min in the furnace.

Results: The DSC spectrum of the crystal form A of the compound of Formula (I) and fumaric acid is shown in FIG. 1, where the crystal form A has a melting endothermic peak around 274° C., which is the melting point of the crystal form A. Thus, it can be seen that the crystal form A has a high melting point and good thermodynamic stability.

3. Thermogravimetric Analysis (TGA) Spectrum Determination Conditions and Data

The TGA spectrum of the crystal form A of the compound of Formula (I) and fumaric acid was obtained in the following manner:

A thermogravimetric analyzer TA Discovery 55 (TA, US) was used. 2 mg to 5 mg of the sample was placed in an equilibrated open aluminum sample pan and automatically weighed in a TGA oven. The sample was heated to the final temperature at a rate of 10° C./min with a nitrogen purge rate of 60 mL/min at the sample and 40 mL/min at the balance.

Results: The TGA spectrum of the crystal form A of the compound of Formula (I) and fumaric acid is shown in FIG. 1, which shows that the crystal form A has basically no weight loss during the process of being heated to 150° C., and may decompose at a temperature higher than 240° C., indicating that the crystal form A is an anhydrous crystal form or has no solvent adsorbed.

4. Dynamic Vapor Sorption (DVS) Analysis

Dynamic vapor sorption analysis was performed using DVS Intrinsic (SMS, UK). The analysis adopted a gradient mode, the humidity change was 50%, 95%, 0%, and 50% in sequence, the humidity change of each gradient in the range from 0% to 90% was 10%, and the end point of the gradient was determined by dm/dt method. The end point of the gradient was determined in response to the dm/dt being less than 0.002% and maintained for 10 minutes.

Figure 2:
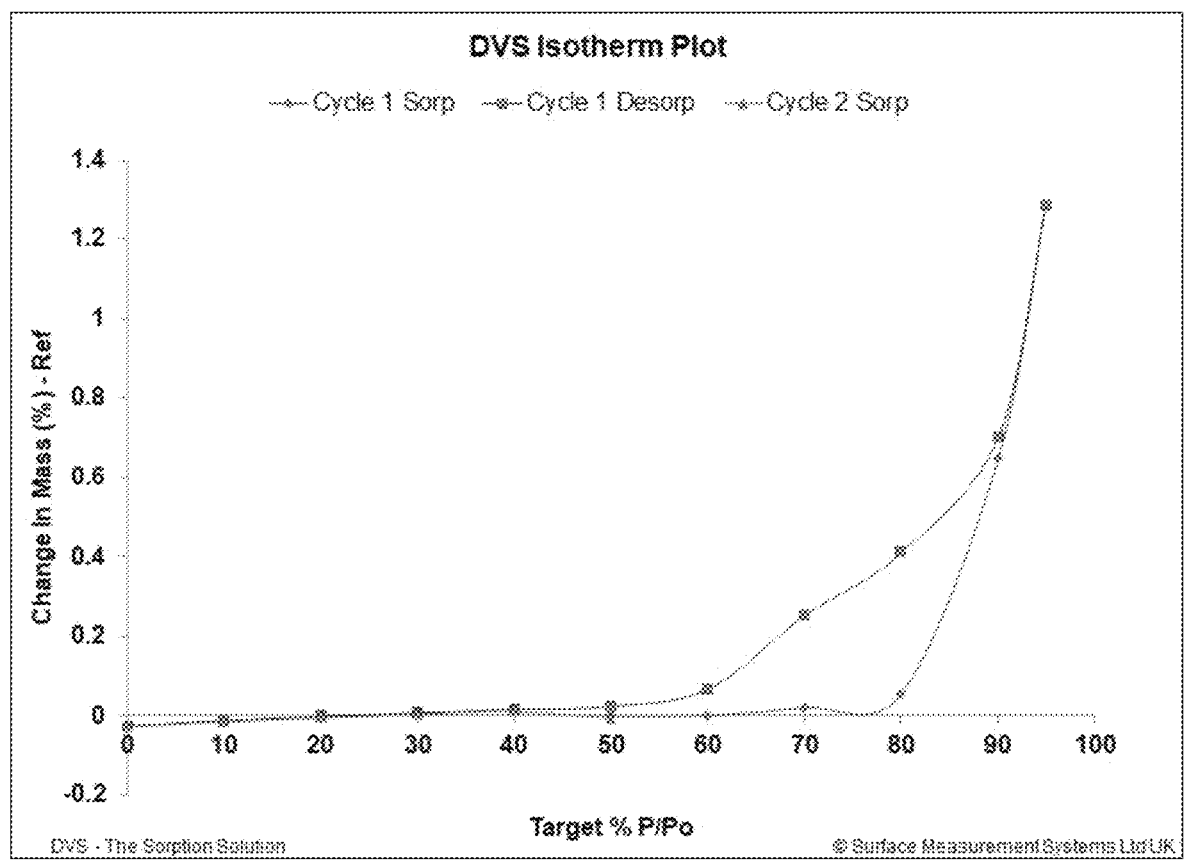
FIG. 2 shows a dynamic vapor sorption (DVS) spectrum of the crystal form A of the compound of Formula (I) and fumaric acid.
Figure 3:
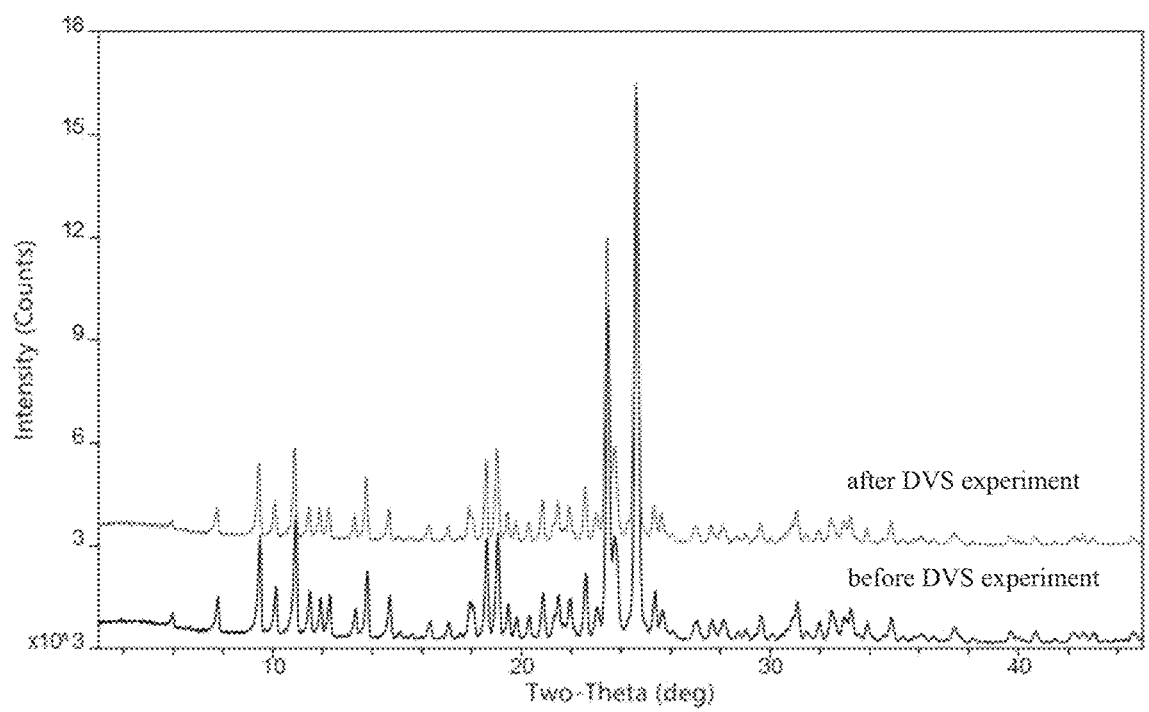
FIG. 3 is a comparison diagram of X-ray powder diffraction (XRPD) patterns of the crystal form A of the compound of Formula (I) and fumaric acid before and after DVS experiment.

Results: The DVS results are shown in FIG. 2; the weight loss was 0.02% at 0% RH, and the weight gain was 0.06% at 80% RH, the sample had almost no hygroscopicity. The comparison between the XRPD patterns of the crystal form A before and after DVS experiment is as shown in FIG. 3. The results show that the crystal form A is very stable, is not prone to crystalline transformation, and is not prone to moisture absorption.

In addition, the inventors also investigated the stability of the crystal form A under conditions of the influencing factor experiment and the accelerated stability experiment, and the results is as follows:

The crystal form A of the compound of Formula (I) and fumaric acid was stable under the conditions of high temperature, high humidity, and light irradiation, and maintained stable appearance and purity within 30 days.

The crystal form A of the compound of Formula (I) and fumaric acid was stable at 40° C. and 75% relative humidity (RH), and maintained stable appearance and purity with no dissociation or crystalline transformation within 2 months. This indicates that the crystal form A has very good stability, which is conducive to the production, transportation, and storage of drugs and ensures the effectiveness and safety of drug use.

On this basis, the inventors further studied particle size parameters of the active pharmaceutical ingredient (API) and investigated the influence of the particle size of the active pharmaceutical ingredient on the effect(s) of preparations containing the same.

Examples of API Production, API-Containing Preparations, and Effects

III. Production Examples of API

A solid form (45 g) of (6E)-6-[(6-chloro-2-methyl-2H-indazol-5-yl)imino]-3-[(1-methyl-1H-1,2,4-triazol-3yl) methyl]-1-(2,4,5-trifluorobenzyl)-1,3,5-triazinane-2,4-dione fumaric acid was added to 450 mL of acetone to form a suspension. According to the conditions listed in the following table, the suspension was heated to a temperature in the range form 55° C. to 70° C., under reflux, and then cooled to a temperature in the range form 20° C. to 30° C., while stirring. Finally, the suspension was separated to obtain a solid. The obtained solid was vacuum-dried to give a series of white solids, i.e., APIs 1 to 17 (42.8 g to 43.7 g) containing the crystal form A of the compound and fumaric acid were obtained, and these APIs have the particle size shown in the table below.

| | Specific reaction temperature, stirring conditions, and particle size ($D_{50}$ and/or $D_{90}$) of the resulting APIs | | | | |
|---|---|---|---|---|---|
| No. | Reaction temperature | Stirring rate | Stirring time | Particle size $D_{50}$ of API | Particle size $D_{90}$ of API |
| API 1 | Heated to 65° C. | 60 rpm | Heated and stirred for 1 h | 28.9 μm | 58.6 μm |
| | Cooled to 30° C. | | Cooled and stirred for 4 h | | |
| API 2 | Heated to 60° C. | 140 rpm | Heated and stirred for 1 h | 20.3 μm | 40.1 μm |
| | Cooled to 25° C. | | Cooled and stirred for 5 h | | |
| API 3 | Heated to 55° C. | 280 rpm | Heated and stirred for 2 h | 8.4 μm | 10.2 μm |
| | Cooled to 20° C. | | Cooled and stirred for 6 h | | |
| API 4 | Heated to 65° C. | 75 rpm | Heated and stirred for 1 h | 23.5 μm | 46.7 μm |
| | Cooled to 25° C. | | Cooled and stirred for 5 h | | |
| API 5 | Heated to 60° C. | 180 rpm | Heated and stirred for 1 h | 18.6 μm | 34.2 μm |
| | Cooled to 20° C. | | Cooled and stirred for 5 h | | |
| API 6 | Heated to 55° C. | 240 rpm | Heated and stirred for 2 h | 8.9 μm | 15.6 μm |
| | Cooled to 20° C. | | Cooled and stirred for 6 h | | |
| API 7 | Heated to 65° C. | 95 rpm | Heated and stirred for 1 h | 22.3 μm | 45.5 μm |
| | Cooled to 25° C. | | Cooled and stirred for 5 h | | |
| API 8 | Heated to 60° C. | 150 rpm | Heated and stirred for 1 h | 20.1 μm | 40.7 μm |
| | Cooled to 25° C. | | Cooled and stirred for 5 h | | |
| API 9 | Heated to 55° C. | 260 rpm | Heated and stirred for 2 h | 8.8 μm | 10.4 μm |
| | Cooled to 20° C. | | Cooled and stirred for 6 h | | |

-continued

Specific reaction temperature, stirring conditions, and particle size ($D_{50}$ and/or $D_{90}$) of the resulting APIs

| No. | Reaction temperature | Stirring rate | Stirring time | Particle size $D_{50}$ of API | Particle size $D_{90}$ of API |
|---|---|---|---|---|---|
| API 10 | Heated to 60° C. | 105 rpm | Heated and stirred for 1 h | 22.1 μm | 43.4 μm |
| | Cooled to 20° C. | | Cooled and stirred for 4 h | | |
| API 11 | Heated to 60° C. | 120 rpm | Heated and stirred for 1 h | 20.6 μm | 42.7 μm |
| | Cooled to 20° C. | | Cooled and stirred for 4 h | | |
| API 12 | Heated to 55° C. | 300 rpm | Heated and stirred for 2 h | 8.3 μm | 10.9 μm |
| | Cooed to 20° C. | | Cooled and stirred for 6 h | | |
| API 13 | Heated to 65° C. | 85 rpm | Heated and stirred for 1 h | 22.4 μm | 48.9 μm |
| | Cooled to 25° C. | | Cooled and stirred for 5 h | | |
| API 14 | Heated to 60° C. | 130 rpm | Heated and stirred for 1 h | 20.5 μm | 41.3 μm |
| | Cooled to 20° C. | | Cooled and stirred for 6 h | | |
| API 15 | Heated to 55° C. | 210 rpm | Heated and stirred for 1 h | 10.2 μm | 15.8 μm |
| | Cooled to 20° C. | | Cooled and stirred for 5 h | | |
| API 16 | Heated to 70° C. | 30 rpm | Heated and stirred for 0.5 h | 38.3 μm | 70.5 μm |
| | Cooled to 30° C. | | Cooled and stirred for 3 h | | |
| API 17 | Heated to 70° C. | 40 rpm | Heated and stirred for 0.5 h | 35.4 μm | 65.7 μm |
| | Cooled to 30° C. | | Cooled and stirred for 3 h | | |

Figure 4:
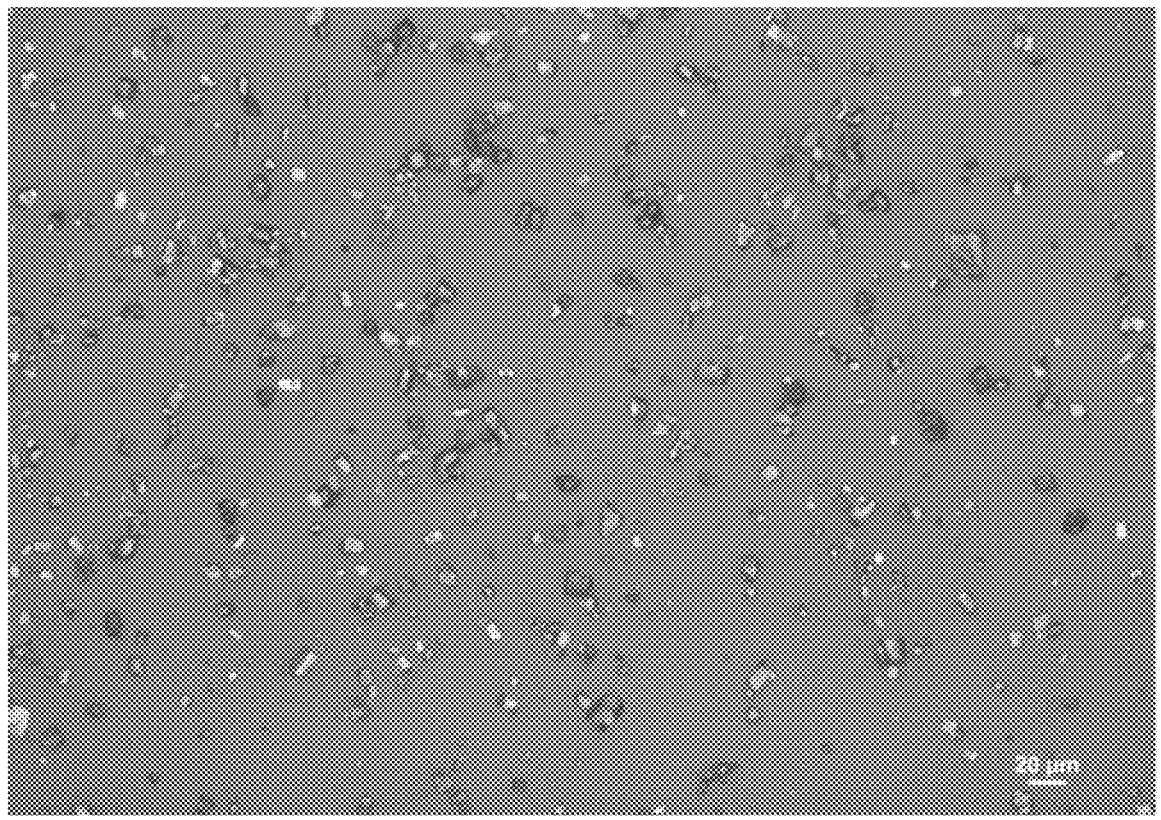
FIG. 4 shows a polarizing light microscope (PLM) image of an active pharmaceutical ingredient (API) 6 including the crystal form A of the compound of Formula (I) and fumaric acid prepared in an example of the present disclosure.

By taking a small amount of the APIs (for example, API 6) prepared in the examples of the present disclosure and placing them on a glass slide, the morphology of these APIs was observed through a polarizing microscope (Nikon Ci-POL, Nikon, JP). The polarizing microscope (PLM) image of the API 6 is shown in FIG. 4.

Figure 5:
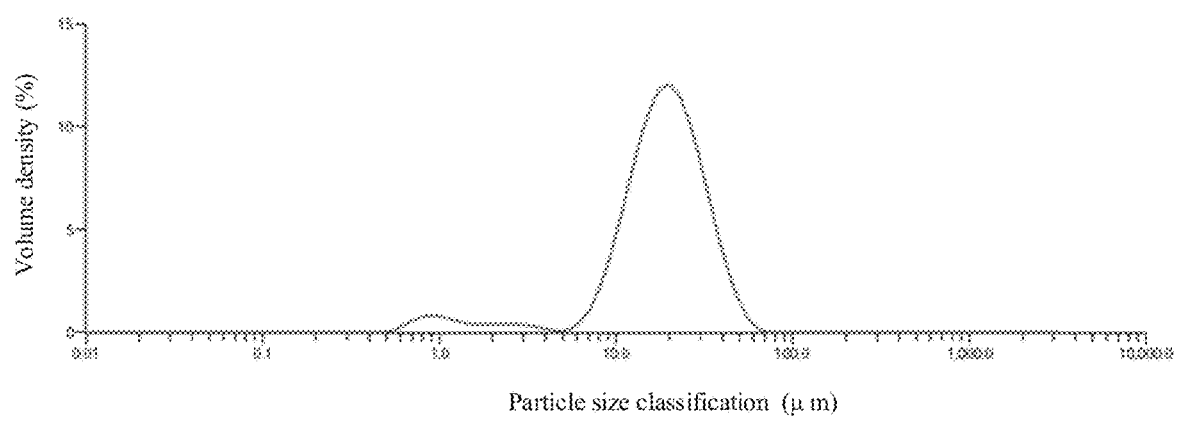
FIG. 5 shows a particle size distribution diagram of an active pharmaceutical ingredient (API) 5 containing the crystal form A of the compound of Formula (I) and fumaric acid prepared in the example of the present disclosure, in which $D_{50}$ is 18.6 μm and $D_{90}$ is 34.2 μm.

The particle size distribution of the APIs prepared in the examples of the present disclosure was determined by using a laser particle size analyzer Mastersizer 3000 (Malvern Panalytical, UK). Specifically, about 20 mg of the API (for example, API 5) prepared in the example of the present disclosure was taken, dispersed in 8 mL of n-heptane, sonicated for 10 seconds, added to a sample dispersion unit until the shading degree was in the range from 10% to 20%, and then measured. The stirring speed of the dispersion chamber was 2000 rpm, and the duration was 10 s. The particle size distribution diagram of the API 5 is shown in FIG. 5.

On the basis that the APIs within the specific particle size range were obtained, the inventors further studied preparations comprising the API and effects thereof.

IV. Preparation Examples

In the preparation examples, preparations 1 to 17 were obtained according to the methods and parameters described below.

Production of Preparations 1, 2, 3 and 16:

| Components | Content (%) | Preparation 1 | Preparation 2 | Preparation 3 | Preparation 16 |
|---|---|---|---|---|---|
| API | 33.33% | 25.0 g $D_{50}$ 28.9 μm $D_{90}$ 58.6 μm | 25.0 g $D_{50}$ 20.3 μm $D_{90}$ 40.1 μm | 25.0 g $D_{50}$ 8.4 μm $D_{90}$ 10.2 μm | 25.0 g $D_{50}$ 38.3 μm $D_{90}$ 70.5 μm |
| Microcrystalline cellulose | 45.81% | 34.3575 g | 34.3575 g | 34.3575 g | 34.3575 g |
| Lactose | 12.36% | 9.27 g | 9.27 g | 9.27 g | 9.27 g |
| Hydroxypropyl cellulose | 2% | 1.5 g | 1.5 g | 1.5 g | 1.5 g |
| Croscarmellose sodium | 2% | 1.5 g | 1.5 g | 1.5 g | 1.5 g |
| Colloidal silica | 3% | 2.25 g | 2.25 g | 2.25 g | 2.25 g |
| Magnesium stearate | 1.5% | 1.13 g | 1.13 g | 1.13 g | 1.13 g |

Production Method:

(1) API (the active ingredient, i.e., API 1, 2, 3, or 16 containing the crystal form A of the compound of Formula (I) and fumaric acid) was mixed uniformly with microcrystalline cellulose;

(2) Lactose, hydroxypropyl cellulose, croscarmellose sodium, and colloidal silica were added to the mixture obtained in step (1) and mixed uniformly;

(3) Wet granulation was performed on the mixture obtained in step (2) with 34.9874 g of purified water, and cycled, followed by sieving through a 40 to 60-mesh sieve, and drying at 60° C. for 2 hours;

(4) The particles obtained in step (3) were mixed uniformly with magnesium stearate;

(5) The mixture obtained in step (4) was tableted, with 9.5 mm round punch, a controlled average weight difference ±3%, and tablet hardness in a range from 70N to 80N, to obtain tablets with a weight of 375 mg per tablet.

Production of Preparations 4, 5, 6 and 17

| Component | Content (%) | Preparation 4 | Preparation 5 | Preparation 6 | Preparation 17 |
|---|---|---|---|---|---|
| API | 40.64% | 30.48 g $D_{50}$ 23.5 μm $D_{90}$ 46.7 μm | 30.48 g $D_{50}$ 18.6 μm $D_{90}$ 34.2 μm | 30.48 g $D_{50}$ 8.9 μm $D_{90}$ 15.6 μm | 30.48 g $D_{50}$ 35.4 μm $D_{90}$ 65.7 μm |
| Microcrystalline cellulose | 38.5% | 28.875 g | 28.875 g | 28.875 g | 28.875 g |
| Pregelatinized starch | 12.36% | 9.27 g | 9.27 g | 9.27 g | 9.27 g |
| Copovidone | 2% | 1.5 g | 1.5 g | 1.5 g | 1.5 g |
| Croscarmellose sodium | 2% | 1.5 g | 1.5 g | 1.5 g | 1.5 g |
| Colloidal silica | 3% | 2.25 g | 2.25 g | 2.25 g | 2.25 g |
| Magnesium stearate | 1.5% | 1.13 g | 1.13 g | 1.13 g | 1.13 g |

Production Method:

(1) API (the active ingredient, i.e., API 4, 5, 6, or 17 containing the crystal form A of the compound of Formula (I) and fumaric acid) was mixed uniformly with microcrystalline cellulose;

(2) Pregelatinized starch, copovidone, croscarmellose sodium, and colloidal silica were added to the mixture obtained in step (1) and mixed uniformly;

(3) Granulation was performed on the mixture obtained in step (2) with a dry granulator, and cycled, followed by sieving through a 40 to 60-mesh sieve;

(4) The particles obtained in step (3) were mixed with magnesium stearate;

(5) The mixture obtained in step (4) was tableted, with 9.5 mm round punch, a controlled average weight difference ±3%, and tablet hardness in a range from 70N to 80N, to obtain tablets with a weight of 375 mg per tablet.

Production of preparations 7, 8, and 9

| Component | Content (%) | Preparation 7 | Preparation 8 | Preparation 9 |
|---|---|---|---|---|
| API | 20% | 1.8 g $D_{50}$ 22.3 μm $D_{90}$ 45.5 μm | 1.8 g $D_{50}$ 20.1 μm $D_{90}$ 40.7 μm | 1.8 g $D_{50}$ 8.8 μm $D_{90}$ 10.4 μm |
| Lactose | 57% | 5.13 g | 5.13 g | 5.13 g |
| Microcrystalline cellulose | 21% | 1.89 g | 1.89 g | 1.89 g |
| Sodium dodecyl sulfate | 2% | 0.18 g | 0.18 g | 0.18 g |

Production Method:

(1) API (the active ingredient, i.e., API 7, 8, or 9 containing the crystal form A of the compound of Formula (I) and fumaric acid) was mixed uniformly with lactose;

(2) Microcrystalline cellulose and sodium lauryl sulfate were added to the mixture obtained in step (1) and mixed uniformly;

(3) The mixture obtained in step (2) was ground into fine powder;

(4) The fine powder obtained in step (3) was sieved through a 100 to 120-mesh sieve, and packed into a packaging material (such as a small bag) to obtain powders or dry suspensions with a weight of 375 mg per bag.

Production of preparations 10, 11, and 12

| Component | Content (%) | Preparation 10 | Preparation 11 | Preparation 12 |
|---|---|---|---|---|
| API | 16.67% | 1.5 g $D_{50}$ 22.1 μm $D_{90}$ 43.4 μm | 1.5 g $D_{50}$ 20.6 μm $D_{90}$ 42.7 μm | 1.5 g $D_{50}$ 8.3 μm $D_{90}$ 10.9 μm |
| Lactose | 60.33% | 5.43 g | 5.43 g | 5.43 g |
| Microcrystalline cellulose | 21% | 1.89 g | 1.89 g | 1.89 g |
| Sodium dodecyl sulfate | 2% | 0.18 g | 0.18 g | 0.18 g |

Production Method:

(1) API (the active ingredient, i.e., API 10, 11, or 12 containing the crystal form A of the compound of Formula (I) and fumaric acid) was mixed uniformly with lactose;

(2) Microcrystalline cellulose and sodium lauryl sulfate were added to the mixture obtained in step (1) and mixed uniformly;

(3) The mixture obtained in step (2) was ground into fine powder;

(4) The fine powder obtained in step (3) was sieved through a 100 to 120-mesh sieve, and packed into a packaging material (such as a small bag) to obtain powders or dry suspensions with a weight of 375 mg per bag.

Production of preparations 13, 14, and 15

| Component | Content (%) | Preparation 13 | Preparation 14 | Preparation 15 |
|---|---|---|---|---|
| API | 60% | 4.5 g $D_{50}$ 22.4 μm $D_{90}$ 48.9 μm | 4.5 g $D_{50}$ 20.5 μm $D_{90}$ 41.3 μm | 4.5 g $D_{50}$ 10.2 μm $D_{90}$ 15.8 μm |
| Mannitol | 22% | 1.65 g | 1.65 g | 1.65 g |
| Microcrystalline cellulose | 15% | 1.125 g | 1.125 g | 1.125 g |
| Sodium dodecyl sulfate | 3% | 0.225 g | 0.225 g | 0.225 g |

Production Method:

(1) API (the active ingredient, i.e., API 13, 14, or 15 containing the crystal form A of the compound of Formula (I) and fumaric acid) was mixed uniformly with mannitol;

(2) Microcrystalline cellulose and sodium lauryl sulfate were added to the mixture obtained in step (1) and mixed uniformly;

(3) The mixture obtained in step (2) was ground into fine powder;

(4) The fine powder obtained in step (3) was sieved through a 100 to 120-mesh sieve, and packed into a packaging material (such as a small bag) to obtain powders or dry suspensions with a weight of 375 mg per bag.

V. Examples of Effects of the Preparations

1. In Vitro Dissolution Experiment

The experimental method is as follows: the Paddle Apparatus Method was used, the rotation speed was 75 rpm, and 900 ml of dissolution medium was used. The dissolution curves of the preparations 1 to 6, 16, and 17 of the present disclosure in the dissolution medium, namely purified water pH 1.2+0.2% Tween 80, were measured, respectively. At 5 min, 10 min, 15 min, 30 min, 45 min, and 60 min, an appropriate amount of the dissolution solution was taken and filtered, and the subsequent filtrate was taken as the test solution to determine the in vitro dissolution.

The test results are shown in the following table:

| | Dissolution | | | | | | | |
|---|---|---|---|---|---|---|---|---|
| Time | Preparation 1 | Preparation 2 | Preparation 3 | Preparation 16 | Preparation 4 | Preparation 5 | Preparation 6 | Preparation 17 |
| 5 min | 52.0% | 67.7% | 67.9% | 36.7% | 52.5% | 62.1% | 66.5% | 44.2% |
| 10 min | 68.2% | 84.5% | 85.7% | 55.8% | 69.3% | 83.4% | 87.0% | 61.5% |
| 15 min | 76.2% | 90.5% | 92.0% | 67.0% | 76.8% | 91.0% | 94.4% | 67.8% |
| 30 min | 87.2% | 95.3% | 95.4% | 73.2% | 87.4% | 95.2% | 98.3% | 74.1% |
| 45 min | 91.0% | 96.0% | 96.8% | 76.1% | 92.0% | 95.6% | 98.1% | 77.0% |
| 60 min | 93.3% | 96.9% | 97.7% | 82.4% | 94.2% | 97.3% | 98.3% | 83.9% |

Conclusion: In the dissolution medium of purified water pH 1.2+0.2% Tween 80, the preparations 1 to 6 of the present disclosure have higher dissolution rates and higher in vitro dissolutions, while preparations 16 and 17 have lower dissolution rates and relatively lower in vitro dissolutions.

2. Investigation of Main Parameters of Tablet(s)

This study focused on investigation whether sticking or picking phenomenon occurred during the tableting process of the Preparations 1 to 6, 16, and 17 of the present disclosure, as well as the friability of the tablets. Specifically, under the same conditions of tableting (including temperature, humidity, etc. during tableting), whether sticking or picking phenomenon occurred during the tableting process was observed with naked eyes, and it was stipulated according to the 2020 edition of the Chinese Pharmacopoeia (Part Four, Tablet friability test method) that for each preparation, 18 tablets prepared according to Preparation examples 1 and 2 were taken and were tested with a tablet friability tester (CS-3 friability tester, purchased from Tianjin Tuo Pu Instrument Co., Ltd.) to measure the friability parameter (i.e., percent weight loss).

The specific results are shown in the following table:

| Preparation No. | Sticking or picking phenomenon | Friability |
|---|---|---|
| Preparation 1 | — | 0.8% |
| Preparation 2 | — | 0.4% |
| Preparation 3 | + | 0.2% |
| Preparation 16 | + | 3.1% |
| Preparation 4 | — | 0.7% |
| Preparation 5 | — | 0.3% |
| Preparation 6 | + | 0.2% |
| Preparation 17 | ++ | 2.2% |

Sticking Phenomenon:
-- indicates basically no sticking or powder adhesion;
+ indicates a trace amount of powder adhered, and no significant sticking or astringency;
++ indicates significant adhesion on the punching surface;
+++ indicates significant sticking or astringency.

Conclusion: In terms of tablet sticking, Preparations 1 to 6 of the present disclosure basically had no sticking or no significant sticking or picking during the tableting process. In terms of tablet friability, the tablet friability parameters of Preparations 1 to 6 of the present disclosure complied with the stipulations of the Chinese Pharmacopoeia (a weight loss percentage does not exceed 1%), while the tablets of Preparation 16 and 17 did not comply with the stipulations of the Chinese Pharmacopoeia (a weight loss percentage far exceeds 1%). The inventors found that the active pharmaceutical ingredient containing the crystal form A of the compound of Formula (I) and fumaric acid within a specific particle size range (e.g., $D_{50} \leq 30$ μm and/or $5$ μm$\leq D_{90} \leq 60$ μm) was suitable for tableting into tablets.

In addition to the above small-scale production of the API described in the present disclosure, the inventors also explored the pilot-scale production of the API described in the present disclosure in large batches, in which the particle size $D_{90}$ of the obtained API was in the range from about 10 μm to about 60 μm, and/or the particle size $D_{50}$ of the obtained API was in the range from about 5 μm to about 30 μm.

In addition to the particle size parameters of the API and effects thereof on the preparations, the inventors also studied the effects of various excipients and their content changes (i.e., changes in the formulation) on the preparations.

Examples of Pharmaceutical Composition with Optimized Formulation and Effects Thereof VI. Preparation Examples As mentioned above, on the basis that the crystal form A was produced and characterized, the inventors of the present disclosure scaled up the production of the crystal form A, and further explored the formulation of the preparation(s).

Example VI-1

| Bath quantity: 1000 tablets, Strength: API, weighted as free base of the compound, 125 mg per tablet | | |
|---|---|---|
| Components | Amount (g) | Content (%) |
| API | 152.4 | 40.64% |
| Microcrystalline cellulose | 131.25 | 35% |
| Pregelatinized starch | 57.6 | 15.36% |
| Hydroxypropyl cellulose | 7.5 | 2% |
| Croscarmellose Sodium | 7.5 | 2% |
| Colloidal silica | 11.25 | 3% |
| Magnesium stearate | 7.5 | 2% |

Production Method:

(1) Premixing 1: API (the active ingredient, i.e., the crystal form A of (6E)-6-[(6-chloro methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione and fumaric acid) was mixed uniformly with microcrystalline cellulose in percentage by weight;

(2) Premixing 2: pregelatinized starch, hydroxypropyl cellulose, croscarmellose sodium, and colloidal silica were added in percentage by weight to the mixture obtained in step (1) and mixed uniformly;

(3) Granulation: the mixture obtained in step (2) was granulated using a dry granulator, until the granulation rate of 60 mesh or greater reached 70%;

(4) Mixing: the particles obtained in step (3) were mixed uniformly with magnesium stearate in percentage by weight;

(5) Tableting: the mixture obtained in step (4) was tableted, with 9.5 mm round punch, a controlled average weight difference ±3%, and tablet hardness from 70N to 80N, to obtain tablets with a weight of 375 mg per tablet.

Examples VI-2, VI-3, VI-4, and VI-5

| Batch quantity: 200 tablets, Strength: API, weighted as free base of the compound, 125 mg per tablet | | | | | | | | |
|---|---|---|---|---|---|---|---|---|
| | Example VI-2 | | Example VI-3 | | Example VI-4 | | Example VI-5 | |
| Components | Amount (g) | Content (%) | Amount (g) | Content (%) | Amount (g) | Content (%) | Amount (g) | Content (%) |
| API | 30.48 | 40.64% | 30.48 | 40.64% | 30.48 | 40.64% | 30.48 | 40.64% |
| Microcrystalline cellulose | 27.0 | 36% | 24.75 | 33% | 22.88 | 30.5% | 29.63 | 39.5% |

Batch quantity: 200 tablets, Strength: API, weighted as free base of the compound, 125 mg per tablet

| Components | Example VI-2 Amount (g) | Example VI-2 Content (%) | Example VI-3 Amount (g) | Example VI-3 Content (%) | Example VI-4 Amount (g) | Example VI-4 Content (%) | Example VI-5 Amount (g) | Example VI-5 Content (%) |
|---|---|---|---|---|---|---|---|---|
| Pregelatinized starch | 9.27 | 12.36% | 11.52 | 15.36% | 14.90 | 19.86% | 8.52 | 11.36% |
| Hydroxypropyl cellulose | 1.5 | 1% | 3.75 | 5% | 1.13 | 1.5% | 1.88 | 2.5% |
| Croscarmellose sodium | 3.75 | 5% | 1.5 | 1% | 2.25 | 3% | 1.13 | 1.5% |
| Colloidal silica | 2.25 | 3% | 2.25 | 3% | 0.38 | 0.5% | 3.0 | 4% |
| Magnesium stearate | 1.5 | 2% | 1.5 | 2% | 3.0 | 4% | 0.38 | 0.5% |

Production Method:

(1) Premixing 1: API (the active ingredient, i.e., the crystal form A of (6E)-6-[(6-chloro methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione and fumaric acid) was mixed uniformly with microcrystalline cellulose in percentage by weight;

(2) Premixing 2: pregelatinized starch, hydroxypropyl cellulose, croscarmellose sodium, and colloidal silica were added in percentage by weight to the mixture obtained in step (1) and mixed uniformly;

(3) Granulation: the mixture obtained in step (2) was compressed into large sheets which were then smashed and sieved through a 20-mesh sieve;

(4) Mixing: the particles obtained in step (3) were mixed uniformly with magnesium stearate in percentage by weight;

(5) Tableting: the mixture obtained in step (4) was tableted, with 9.5 mm round punch, a controlled average weight difference ±3%, and tablet hardness from 70N to 80N, to obtain tablets with a weight of 375 mg per tablet.

Results: As for the formulations of the preparations of Examples VI-1 to VI-5, there is no picking, sticking, powder adhesion, unstable tablet weight, too high or too low tablet hardness, tablet capping, or other phenomena during the tableting process, and they achieve good compressibility.

The following examples adopt the production method same as or similar to the previous examples VI-2 to VI-5, and used different formulations to obtain tablets with a weight of 375 mg per tablet.

Examples VI-6 and VI-7

Batch Quantity: 200 tablets, Strength: API, weighted as free base of the compound, 125 mg per tablet

| Example VI-6 Components | Example VI-7 Components | Amount (g) | Content (%) |
|---|---|---|---|
| API | API | 30.48 | 40.64% |
| Microcrystalline cellulose | Microcrystalline cellulose | 26.25 | 35% |
| Calcium carbonate | Anhydrous calcium hydrogen phosphate | 11.52 | 15.36% |
| Hydroxypropyl cellulose | Hydroxypropyl cellulose | 1.5 | 2% |
| Croscarmellose sodium | Croscarmellose sodium | 1.5 | 2% |
| Colloidal silica | Colloidal silica | 2.25 | 3% |
| Magnesium stearate | Magnesium stearate | 1.5 | 2% |

Results: Compared with Example VI-1, the difference of the formulations of Examples VI-10 and VI-11 was that the pregelatinized starch, one of the fillers, was replaced with calcium carbonate or anhydrous calcium hydrogen phosphate. It turned out that as for the formulations of Examples VI-6 and VI-7, there is a picking phenomenon during the tableting process, resulting in relatively poor compressibility.

Examples VI-8 and VI-9

Batch Quantity: 200 tablets, Strength: API, weighted as free base of the compound, 125 mg per tablet

| Example VI-8 Components | Example VI-9 Components | Amount (g) | Content (%) |
|---|---|---|---|
| API | API | 30.48 | 40.64% |
| Microcrystalline cellulose | Microcrystalline cellulose | 26.25 | 35% |
| Pregelatinized starch | Pregelatinized starch | 11.52 | 15.36% |
| Polyvinylpyrrolidone | Hydroxyethyl cellulose | 1.5 | 2% |
| Croscarmellose sodium | Croscarmellose sodium | 1.5 | 2% |
| Colloidal silica | Colloidal silica | 2.25 | 3% |
| Magnesium stearate | Magnesium stearate | 1.5 | 2% |

Results: Compared with Example VI-1, the difference of the formulations of Examples VI-8 and VI-9 was that hydroxypropyl cellulose, as a binder, was replaced with polyvinylpyrrolidone or hydroxyethyl cellulose. It turned out that as for the preparation formulations of Examples VI-8 and VI-9, there is a sticking phenomenon during the tableting process, resulting in relatively poor compressibility.

Examples VI-10 and VI-11

Batch Quantity: 200 tablets, Strength: API, weighted as free base of the compound, 125 mg per tablet

| Components | Example VI-10 Amount (g) | Example VI-10 Content (%) | Example VI-11 Amount (g) | Example VI-11 Content (%) |
|---|---|---|---|---|
| API | 30.48 | 40.64% | 30.48 | 40.64% |
| Microcrystalline cellulose | 27.23 | 36.3% | 26.25 | 35% |
| Pregelatinized starch | 11.52 | 15.36% | 9.05 | 12.06% |
| Hydroxypropyl cellulose | 0.53 | 0.7% | 3.98 | 5.3% |
| Croscarmellose sodium | 1.5 | 2% | 1.5 | 2% |
| Colloidal silica | 2.25 | 3% | 2.25 | 3% |
| Magnesium stearate | 1.5 | 2% | 1.5 | 2% |

Results: Compared with Example VI-1, the difference of the formulations of Examples VI-10 and VI-11 was that the Results: Compared with Example VI-1, the main difference of the formulations of Examples VI-10 and VI-11 was that the content of hydroxypropyl cellulose as a binder was adjusted to 0.7% and 5.3%, respectively. It turned out that the formulation of Example VI-10 had a too low tablet harness (20N) and the formulation of Example VI-11 had a too high tablet hardness (95N) during the tableting process, resulting in relatively poor compressibility.

Examples VI-12 and VI-13

Batch Quantity: 200 tablets, Specification: API, weighted as free base of the compound, 125 mg per tablet

| | Example VI-12 | | Example VI-13 | |
|---|---|---|---|---|
| Components | Amount (g) | Content (%) | Amount (g) | Content (%) |
| API | 30.48 | 40.64% | 30.48 | 40.64% |
| Microcrystalline cellulose | 27.15 | 36.2% | 23.63 | 31.5% |
| Pregelatinized starch | 11.52 | 15.36% | 11.52 | 15.36% |
| Hydroxypropyl cellulose | 1.5 | 2% | 1.5 | 2% |
| Croscarmellose sodium | 0.6 | 0.8% | 4.13 | 5.5% |
| Colloidal silica | 2.25 | 3% | 2.25 | 3% |
| Magnesium stearate | 1.5 | 2% | 1.5 | 2% |

Results: Compared with Example VI-1, the main difference of the formulations of Examples VI-12 and VI-13 was that the content of croscarmellose sodium as a disintegrant was adjusted to 0.8% and 5.5%, respectively. It turned out that as for the formulations of Examples VI-12 and VI-13, there is no phenomena of picking, sticking, powder adhesion, unstable tablet weight, too high or too low tablet hardness, tablet capping, or the like during the tableting process, and they achieve good compressibility. Nevertheless, the formulations of examples VI-12 and VI-13 result in defects in dissolution, which will be described in the section "VII. Examples of effects of the preparation(s)".

Examples VI-14 and VI-15

Batch Quantity: 200 tablets, Strength: API, weighted as free base of the compound, 125 mg per tablet

| | Example VI-14 | | Example VI-15 | |
|---|---|---|---|---|
| Components | Amount (g) | Content (%) | Amount (g) | Content (%) |
| API | 30.48 | 40.64% | 30.48 | 40.64% |
| Microcrystalline cellulose | 26.25 | 35% | 26.25 | 35% |
| Pregelatinized starch | 13.55 | 18.06% | 10.40 | 13.86% |
| Hydroxypropyl cellulose | 1.5 | 2% | 1.5 | 2% |
| Croscarmellose sodium | 1.5 | 2% | 1.5 | 2% |
| Colloidal silica | 0.23 | 0.3% | 3.38 | 4.5% |
| Magnesium stearate | 1.5 | 2% | 1.5 | 2% |

Results: Compared with Example VI-1, the main difference of the formulations of Examples VI-14 and VI-15 was that the content of colloidal silica as a glidant was adjusted to 0.3% and 4.5%, respectively. It turned out that as for the formulations of Examples VI-14 and VI-15, there is a phenomenon of unstable tablet weight during the tableting process, resulting in relatively poor compressibility.

Examples VI-16 and VI-17

Batch Quantity: 200 tablets, Strength: API, weighted as free base of the compound, 125 mg per tablet

| | Example VI-16 | | Example VI-17 | |
|---|---|---|---|---|
| Components | Amount (g) | Content (%) | Amount (g) | Content (%) |
| API | 30.48 | 40.64% | 30.48 | 40.64% |
| Microcrystalline cellulose | 27.45 | 36.6% | 24.6 | 32.8% |
| Pregelatinized starch | 11.52 | 15.36% | 11.52 | 15.36% |
| Hydroxypropyl cellulose | 1.5 | 2% | 1.5 | 2% |
| Croscarmellose sodium | 1.5 | 2% | 1.5 | 2% |
| Colloidal silica | 2.25 | 3% | 2.25 | 3% |
| Magnesium stearate | 0.3 | 0.4% | 3.15 | 4.2% |

Figure 6:
FIG. 6 shows a powder adhesion phenomenon occurring during the tableting process of the preparation formulation of Example VI-16.

Results: Compared with Example VI-1, the main difference of the formulations of Examples VI-16 and VI-17 was that the content of magnesium stearate as a lubricant was adjusted to 0.4% and 4.2%, respectively. It turned out that as for the formulations of Examples VI-16 and VI-17, there is phenomena of powder adhesion, sticking, and picking during the tableting process, resulting in relatively poor compressibility. In particular, as the formulation of Example VI-16, the phenomenon of powder adhesion during the tableting process is shown in FIG. 6.

Examples VI-18 and VI-19

Batch Quantity: 200 tablets, Strength: API, weighted as free base of the compound, 125 mg per tablet

| | Example VI-18 | | Example VI-19 | |
|---|---|---|---|---|
| Components | Amount (g) | Content (%) | Amount (g) | Content (%) |
| API | 30.48 | 40.64% | 30.48 | 40.64% |
| Microcrystalline cellulose | 21.75 | 29% | 30.75 | 41% |
| Pregelatinized starch | 16.02 | 21.36% | 7.02 | 9.36% |
| Hydroxypropyl cellulose | 1.5 | 2% | 1.5 | 2% |
| Croscarmellose sodium | 1.5 | 2% | 1.5 | 2% |
| Colloidal silica | 2.25 | 3% | 2.25 | 3% |
| Magnesium stearate | 1.5 | 2% | 1.5 | 2% |

Figure 7:
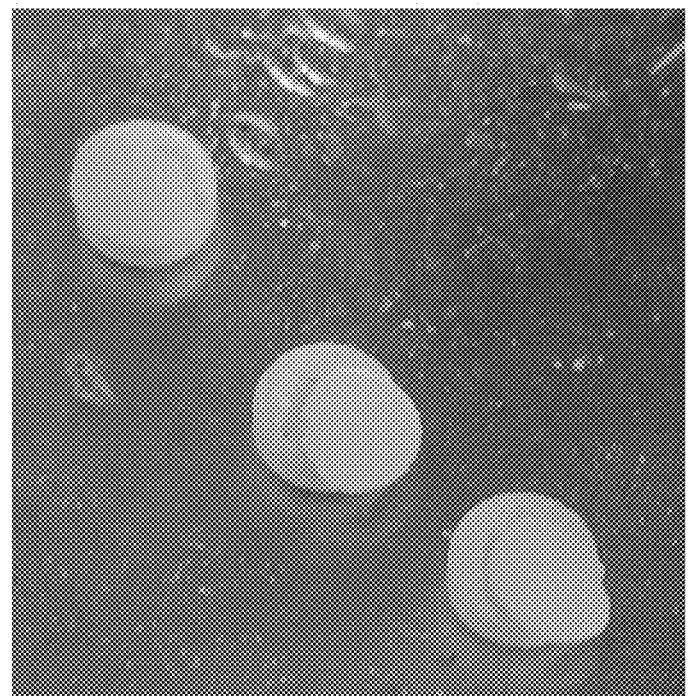
FIG. 7 shows a tablet capping phenomenon occurring during the tableting process of the preparation formulation of Example VI-18.

Results: Compared with Example VI-1, the main difference of the formulations of Examples VI-18 and VI-19 was that the weight ratio of microcrystalline cellulose and pregelatinized starch as the fillers were adjusted to 1.3:1 and 4.4:1, respectively. It turned out that as for the formulations of Examples VI-18 and VI-19, there is a phenomenon of tablet capping in the tableting process, resulting in relatively poor compressibility. In particular, as for the formulation of Example VI-18, the phenomenon of tablet capping during the tableting process was shown in FIG. 7.

As illustrated in Examples VI-1 to VI-19, the above formulations of the pharmaceutical compositions were mainly obtained through the production method comprising dry granulation, and the effects of the changes in formulation parameters (i.e., the types and/or contents of components) on the compressibility of the tablets were also established on the basis of dry granulation. In order to explore the tablets produced by a production method comprising wet granulation, the inventors also studied the effects of the changes in exemplary formulation parameters of the preparations produced by the production method comprising wet granulation on the compressibility and/or dissolution of the tablets, as illustrated in the results of Examples VI-20 to VI-29 below.

Example VI-20

| Batch Quantity: 1000 tablets, Strength: API, weighted as free base of the compound, 125 mg per tablet | | |
|---|---|---|
| Components | Amount (g) | Content (%) |
| API | 152.4 | 40.64% |
| Microcrystalline cellulose | 142.5 | 38% |
| D-mannitol | 46.35 | 12.36% |
| Hydroxypropyl cellulose | 7.5 | 2% |
| Croscarmellose sodium | 7.5 | 2% |
| Colloidal silica | 11.25 | 3% |
| Magnesium stearate | 7.5 | 2% |

Production Method:

Premixing 1: API (the active ingredient, i.e., the crystal form A of (6E)-6-[(6-chloro methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione and fumaric acid) was mixed uniformly with microcrystalline cellulose in percentage by weight;

(2) Premixing 2: D-mannitol, hydroxypropyl cellulose, croscarmellose sodium, and colloidal silica were added in percentage by weight to the mixture obtained in step (1) and mixed uniformly;

(3) Granulation: the mixture obtained in step (2) was granulated in a wet granulator using purified water, followed by sieving through a 20-mesh sieve, and drying at 60° C. for 2 h;

(4) Mixing: the particles obtained in step (3) were mixed uniformly with magnesium stearate in percentage by weight;

(5) Tableting: the mixture obtained in step (4) was tableted, with 9.5 mm round punch, a controlled average weight difference ±3%, tablet hardness of 70 N to 80 N, to obtain tablets with a weight of 375 mg per tablet.

Results: As for the formulation of Example VI-20, there is no phenomenon of picking, sticking, powder adhesion, unstable tablet weight, too high or too low tablet hardness, tablet capping, or the like during the tableting process, and it achieves good compressibility.

Examples VI-21 to VI-24

| Quantity: 200 tablets, Strength: API, weighted as free base of the compound, 125 mg per tablet | | | | | | | | |
|---|---|---|---|---|---|---|---|---|
| | Example VI-21 | | Example VI-22 | | Example VI-23 | | Example VI-24 | |
| Components | Amount (g) | Content (%) | Amount (g) | Content (%) | Amount (g) | Content (%) | Amount (g) | Content (%) |
| API | 30.48 | 40.64% | 30.48 | 40.64% | 30.48 | 40.64% | 30.48 | 40.64% |
| Microcrystalline cellulose | 30.0 | 40% | 28.5 | 38% | 8.15 | 10.86% | 6.65 | 8.86% |
| D-mannitol | 9.27 | 12.36% | 8.15 | 10.86% | 28.5 | 38% | 33.0 | 44% |
| Hydroxypropyl cellulose | 1.5 | 2% | 0.75 | 1% | 3.75 | 5% | 0.75 | 1% |
| Croscarmellose sodium | 1.5 | 2% | 3.75 | 5% | 0.75 | 1% | 1.88 | 2.5% |
| Colloidal silica | 1.5 | 2% | 1.13 | 1.5% | 0.38 | 0.5% | 3.0 | 4% |
| Magnesium stearate | 0.75 | 1% | 1.5 | 2% | 3.0 | 4% | 0.38 | 0.5% |

Production Method:

(1) Premixing 1: API (the active ingredient, i.e., the crystal form A of (6E)-6-[(6-chloro methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione and fumaric acid) was mixed uniformly with microcrystalline cellulose in percentage by weight;

(2) Premixing 2: D-mannitol, hydroxypropyl cellulose, croscarmellose sodium, and colloidal silica were added in percentage by weight to the mixture obtained in step (1) and mixed uniformly;

(3) Granulation: the mixture obtained in step (2) was manually wet granulated with purified water, followed by sieving through a 20-mesh sieve, and drying at 60° C. for 2 h;

(4) Mixing: the particles obtained in step (3) was mixed uniformly with magnesium stearate in percentage by weight;

(5) Tableting: the mixture obtained in step (4) was tableted, with a 9.5 mm round punch, a controlled average weight difference ±3%, tablet hardness from 70 N to 80 N, to obtain tablets with a weight of 375 mg per tablet.

Results: As for the formulations of Examples VI-21 to VI-24, there is no phenomenon of picking, sticking, powder adhesion, unstable tablet weight, too high or too low tablet hardness, or the like during the tableting process, and they achieve good compressibility.

The following Examples VI-25 to VI-29 adopted substantially the same production methods as Examples VI-21 to VI-24 and different formulations to obtain tablets with a weight of 375 mg per tablet.

Examples VI-25 to VI-27

| Batch Quantity: 200 tablets, Strength: API, weighted as free base of the compound, 125 mg per tablet | | | | | | |
|---|---|---|---|---|---|---|
| | Example VI-25 | | Example VI-26 | | Example VI-27 | |
| Components | Amount (g) | Content (%) | Amount (g) | Content (%) | Amount (g) | Content (%) |
| API | 30.48 | 40.64% | 30.48 | 40.64% | 30.48 | 40.64% |
| Microcrystalline cellulose | 33.0 | 44% | 8.15 | 10.86% | 6.65 | 8.86% |
| D-mannitol | 6.65 | 8.86% | 28.5 | 38% | 33.0 | 44% |
| Hydroxypropyl cellulose | 1.88 | 2.5% | 3.75 | 5% | 0.75 | 1% |

-continued

Batch Quantity: 200 tablets, Strength: API, weighted as free base of the compound, 125 mg per tablet

| Components | Example VI-25 | | Example VI-26 | | Example VI-27 | |
|---|---|---|---|---|---|---|
| | Amount (g) | Content (%) | Amount (g) | Content (%) | Amount (g) | Content (%) |
| Croscarmellose sodium | 0.75 | 1% | 0.75 | 1% | 1.88 | 2.5% |
| Colloidal silica | 1.5 | 2% | 0.38 | 0.3% | 3.23 | 4.3% |
| Magnesium stearate | 0.75 | 1% | 3.15 | 4.2% | 0.15 | 0.2% |

Results: As for the formulation of Example VI-25, there is no phenomenon of picking, sticking, powder adhesion, unstable tablet weight, too high or too low tablet hardness, or the like during the tableting process, and it achieves good compressibility.

Compared with Examples VI-23 and VI-24, the main difference of the formulations of Examples VI-26 and VI-27 was that the contents of the colloidal silica as a glidant and the magnesium stearate as a lubricant were adjusted, respectively. It turned out that as for the formulations of Examples VI-26 and VI-27, there is a phenomenon of powder adhesion, picking, or sticking during the tableting process, resulting in relatively poor compressibility.

Examples VI-28 and VI-29

Batch Quantity: 200 tablets, Strength: API, weighted as free base of the compound, 125 mg per tablet

| Components | Example VI-28 | | Example VI-29 | |
|---|---|---|---|---|
| | Amount (g) | Content (%) | Amount (g) | Content (%) |
| API | 30.48 | 40.64% | 30.48 | 40.64% |
| Microcrystalline cellulose | 33.0 | 44% | 6.27 | 8.36% |
| D-mannitol | 6.27 | 8.36% | 33.0 | 44% |
| Hydroxypropyl cellulose | 1.5 | 2% | 1.5 | 2% |
| Croscarmellose sodium | 1.5 | 2% | 1.5 | 2% |
| Colloidal silica | 1.5 | 2% | 1.5 | 2% |
| Magnesium stearate | 0.75 | 1% | 0.75 | 1% |

Results: Compared with Example VI-21, the main difference of the formulations of Examples VI-28 and VI-29 was that the weight ratio of microcrystalline cellulose and D-mannitol as fillers was adjusted to 5.3:1 and 1:5.3, respectively. It turned out that as for the formulations of Examples VI-28 and VI-29, there is a phenomenon of table capping during the tableting process, resulting in relatively poor compressibility.

For the formulations described in the examples involving wet granulation, in addition to the contents of the glidant and/or the lubricant and the weight ratio of two fillers (i.e., microcrystalline cellulose and D-mannitol) in the formulation, the inventors also investigated other formulation parameters including the type of the filler(s), the type of the binder, and the content of the disintegrant. The results are similar to the effects of changes in formulation parameters of preparations produced by the production method comprising dry granulation on the compressibility and/or dissolution of tablets. That is, 1) the change of the type of the filler (such as D-mannitol) will affect the compressibility of tablets (for example, the phenomenon of picking occurs during the tableting process); 2) the change of the type of the binder (i.e., hydroxypropyl cellulose) and/or the content of the binder exceeding the range defined in the present disclosure will affect the compressibility of tablets (for example, the phenomenon of sticking or the phenomenon of excessively low or high hardness of the tablet(s) occurs during the tableting process); and 3) the content of the disintegrant exceeding the range defined in the present disclosure has no influence on the compressibility of tablets, but causes defects in tablet dissolution.

In order to facilitate the administration for children, the inventors of the present disclosure also explored dosage forms and dosages suitable for children, specifically in Examples VI-30 and VI-31.

Example VI-30

| Components | Amount (g) | Content (%) |
|---|---|---|
| API | 6.005 | 20.32 |
| D-mannitol | 24.349 | 72.68 |
| Sucrose | 1.675 | 5.00 |
| Ascorbic acid | 0.67 | 2.00 |

Production Method:

(1) API (the active ingredient, i.e., the crystal form A of (6E)-6-[(6-chloro-2-methyl-2H-indazol-5-yl)imino]-3-[(1-methyl-1H-1,2,4-triazol-3-yl)methyl]-1-[(2,4,5-trifluorophenyl)methyl]-1,3,5-triazine-2,4-dione and fumaric acid) and mannitol were mixed uniformly in percentage by weight;

(2) Sucrose and ascorbic acid were added in percentage by weight to the mixture obtained in step (1) and mixed uniformly;

(3) The mixture obtained in step (2) was ground into fine powder;

(4) The fine powder obtained in step (3) was sieved through a 120-mesh sieve, and packed into a packaging material (such as a small bag) to obtain powders or dry suspensions.

Example VI-31

| Components | Amount (g) | Content (%) |
|---|---|---|
| API | 6.005 | 20.32 |
| Microcrystalline cellulose | 25.094 | 80.46 |
| Sucrose | 0.67 | 2.00 |
| Ascorbic acid | 0.67 | 2.00 |

Production Method:

(1) API (the active ingredient, i.e., the crystal form A of (6E)-6-[(6-chloro-2-methyl-2H-indazol-5-yl)imino]-3-[(1-methyl-1H-1,2,4-triazol-3-yl)methyl]-1-[(2,4,5-trifluorophenyl)methyl]-1,3,5-triazine-2,4-dione and fumaric acid) and microcrystalline cellulose are mixed uniformly in percentage by weight;

(2) Sucrose and ascorbic acid were added in percentage by weight to the mixture obtained in step (1) and mixed uniformly;

(3) The mixture obtained in step (2) was ground and sieved through a 60-mesh sieve; and (4) The undersize mixture obtained in step (3) was packed into a packaging material (such as gelatin capsules) to obtain capsules.

VII. Examples of Effects of the Preparations

1. In Vitro Dissolution Experiment

The experiment was carried out by the Paddle Apparatus Method, with a rotation speed of 75 rpm, and 900 ml of the dissolution medium. The dissolution curves of the pharmaceutical compositions obtained in Examples VI-1, VI-12, VI-13, and VI-20 in the dissolution medium, namely purified water+0.1% CTAB, were measured, respectively. At 5 min, 10 min, 15 min, 30 min, 45 min, and 60 min, an appropriate amount of the dissolution solution was taken and filtered, and the subsequent filtrate was used as the test solution to determine the in vitro dissolution.

The specific measurement results are shown in the following table:

|  | Dissolution | | | |
| --- | --- | --- | --- | --- |
| Time point | Example VI-1 | Example VI-20 | Example VI-12 | Example VI-13 |
| 5 min | 63.8% | 67.9% | 17.1% | 85.9% |
| 10 min | 83.2% | 84.5% | 26.9% | 92.2% |
| 15 min | 90.1% | 90.5% | 32.7% | 98.0% |
| 30 min | 96.6% | 95.3% | 42.1% | 98.3% |
| 45 min | 97.4% | 96.0% | 47.5% | 98.1% |
| 60 min | 97.6% | 95.9% | 51.2% | 98.3% |

Conclusion: In the dissolution medium of purified water+0.1% CTAB, the dissolutions of the pharmaceutical compositions prepared in Examples VI-1 and VI-20 reached 80% or greater within 30 min and 90% or greater within 60 min. That is, the dissolution rate was high and the in vitro dissolution was high, which can meet the dissolution requirements. In contrast, the dissolution of the pharmaceutical composition prepared in Example VI-12 did not reach 60% within 60 min; although the pharmaceutical composition prepared in Example VI-13 met the dissolution requirements, but a dissolution thereof reached 80% or greater within 5 minutes and 90% or greater within 10 minutes, and the dissolution rate was too high. Therefore, the formulations of Examples VI-12 and VI-13 achieve good compressibility during tableting but result in defects in dissolution.

2. Stability Experiment

The pharmaceutical compositions prepared by representative examples VI-1 and VI-20 were selected and packed using oral high-density polyvinyl chloride bags as inner packaging for testing. Routine accelerated experiments were carried out in a stability test chamber for 1 month and 3 months under the conditions of 40° C.±2° C. and 75%±5% RH, to investigate the influence on the content of involved substances in the tested pharmaceutical compositions.

| Example | Investigated item | | 0 day | 1 month | 3 months |
| --- | --- | --- | --- | --- | --- |
| Example VI-1 | Property | | Off white tablet | Off white tablet | Off white tablet |
|  | Involved substance | Maximum single purity content (%) | 0.07 | 0.07 | 0.07 |
|  |  | Total purity content (%) | 0.23 | 0.23 | 0.23 |
| Example VI-20 | Property | | Off white tablet | Off white tablet | Off white tablet |
|  | Involved substance | Maximum single purity content (%) | 0.07 | 0.07 | 0.08 |
|  |  | Total purity content (%) | 0.23 | 0.23 | 0.24 |

Results: The involved substances in the pharmaceutical compositions produced in Examples VI-1 and VI-20 had no significant changes under the accelerated stability test conditions, which met the requirements of quality standards, indicating that the pharmaceutical compositions of the present disclosure were stable.

The specific examples described above further describe the purpose, technical solutions, and beneficial effects of the present disclosure. It should be understood that the above are only specific embodiments of the present disclosure and are not intended to limit the protection scope of the present disclosure. Any modification, equivalent replacement, improvement, etc. made within the ideas and essence of the present disclosure shall be included in the protection scope of the present disclosure.

What is claimed is:

1. A crystal form comprising a compound of Formula (I) and fumaric acid:

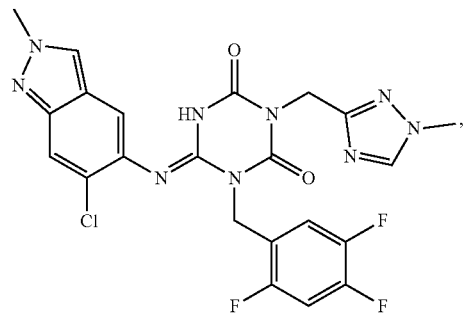

Formula (I)

wherein,
an X-ray powder diffraction pattern of the crystal form obtained by using Cu-Kα radiation comprises at least three peaks selected from the group consisting of 10.94°±0.2° 2θ, 19.06°±0.2° 2θ, 23.50°±0.2° 2θ, and 24.66°±0.2° 2θ.

2. The crystal form according to claim 1, wherein the X-ray powder diffraction pattern comprises at least 9 peaks selected from the group consisting of 10.94°±0.2° 2θ, 19.06°±0.2° 2θ, 23.50°±0.2° 2θ, 24.66°±0.2° 2θ, 9.5°±0.2° 2θ, 13.81°±0.2° 2θ, 18.61°±0.2° 2θ, 22.59°±0.2° 2θ, 23.8°±0.2° 2θ, 7.81°±0.2° 2θ, 10.14°±0.2° 2θ, 11.50°±0.2° 2θ, 11.93°±0.2° 2θ, 12.31°±0.2° 2θ, 14.73°±0.2° 2θ, 20.87°±0.2° 2θ, 21.49°±0.2° 2θ, 21.97°±0.2° 2θ, and 25.39°±0.2° 2θ.

3. The crystal form according to claim 1, wherein the X-ray powder diffraction pattern comprises the following peaks: 10.94°±0.2° 2θ, 19.06°±0.2° 2θ, 23.50°±0.2° 2θ, 24.66°±0.2° 2θ, 9.5°±0.2° 2θ, 13.81°±0.2° 2θ, 18.61°±0.2° 2θ, 22.59°±0.2° 2θ, and 23.8°±0.2° 2θ.

4. The crystal form according to claim 1, wherein in the crystal form, a molar ratio of the compound of Formula (I) to the fumaric acid is about 1:1.

5. The crystal form according to claim 1, wherein the crystal form has a purity greater than or equal to 98%; or a maximum content of a single impurity in the crystal form does not exceed 0.1%.

6. The crystal form according to claim 1, wherein the crystal form comprises:
   a co-crystal of the compound of Formula (I) and the fumaric acid; or
   a fumarate salt of the compound of Formula (I).

7. An active pharmaceutical ingredient, containing the crystal form according to claim 1, wherein the active pharmaceutical ingredient satisfies at least one of the following conditions:

(1) a particle size $D_{90}$ of the active pharmaceutical ingredient ranges from about 5 μm to about 60 μm; and (2) a particle size $D_{50}$ of the active pharmaceutical ingredient does not exceed about 30 μm.

8. The active pharmaceutical ingredient according to claim 7, wherein the particle size $D_{90}$ of the active pharmaceutical ingredient is not smaller than about 10 μm.

9. The active pharmaceutical ingredient according to claim 7, wherein the particle size $D_{50}$ of the active pharmaceutical ingredient is not smaller than about 5 μm.

10. A pharmaceutical composition, comprising
an active ingredient, the active ingredient being the crystal form according to claim 1 or a mixture of the crystal form and an amorphous form of the compound of Formula (I) and the fumaric acid; and
physiologically or pharmaceutically acceptable excipient(s) including one or more selected from the group consisting of filler(s), disintegrant(s), lubricant(s), binder(s), or glidant(s).

11. The pharmaceutical composition according to claim 10, wherein the pharmaceutical composition comprises 15% to 60% by weight of the active ingredient, based on a total weight of the pharmaceutical composition.

12. The pharmaceutical composition according to claim 10, wherein
the filler(s) includes one or more selected from the group consisting of lactose, anhydrous calcium bicarbonate, sugar alcohol(s), cellulose, and starch;
the disintegrant(s) includes one or more selected from the group consisting of crospovidone, croscarmellose sodium, low-substituted hydroxypropyl cellulose, carboxymethyl starch sodium, corn starch, and potato starch;
the lubricant(s) includes one or more selected from the group consisting of magnesium stearate, calcium stearate, zinc stearate, hydrogenated vegetable oil, glyceryl behenate, stearic acid, and sodium stearyl fumarate;
the binder(s) includes one or more selected from the group consisting of hypromellose, hydroxypropyl cellulose, methyl cellulose, hydroxyethyl cellulose, carboxymethyl cellulose, and polyvinylpyrrolidone; and/or
the glidant(s) includes colloidal silica and/or talc.

13. The pharmaceutical composition according to claim 10, wherein
the filler(s) is a mixture of microcrystalline cellulose and D-mannitol or a mixture of microcrystalline cellulose and pregelatinized starch;
the binder(s) is hydroxypropyl cellulose;
the disintegrant(s) is croscarmellose sodium;
the glidant(s) is colloidal silica; and
the lubricant(s) is magnesium stearate.

14. The pharmaceutical composition according to claim 10, wherein the pharmaceutical composition comprises, based on a total weight of the pharmaceutical composition,
30% to 70% by weight of the filler(s);
1% to 5% by weight of the disintegrant(s);
0.5% to 4% by weight of the lubricant(s);
1% to 5% by weight of the binder(s); and
0.5% to 4% by weight of the glidant(s).

15. The pharmaceutical composition according to claim 10, wherein the pharmaceutical composition comprises, based on a total weight of the pharmaceutical composition,
15% to 60% by weight of the active ingredient;
30% to 70% by weight of the filler(s);
1% to 5% by weight of the disintegrant(s);
0.5% to 4% by weight of the lubricant(s);
1% to 5% by weight of the binder(s); and
0.5% to 4% by weight of the glidant(s).

16. The pharmaceutical composition according to claim 13, wherein the pharmaceutical composition comprises, based on a total weight of the pharmaceutical composition,
30% to 70% by weight of the filler(s);
1% to 5% by weight of the disintegrant(s);
0.5% to 4% by weight of the lubricant(s);
1% to 5% by weight of the binder(s); and
0.5% to 4% by weight of the glidant(s).

17. The pharmaceutical composition according to claim 10, wherein the pharmaceutical composition is an oral preparation in a form of a unit dose, and the pharmaceutical composition comprising 1 mg to 500 mg of the active ingredient per unit dose.

18. The pharmaceutical composition according to claim 17, wherein the pharmaceutical composition is an oral preparation in a form of a unit dose, and the pharmaceutical composition comprises 50 mg to 200 mg of the active ingredient per unit dose or comprises 40 mg to 170 mg of a free base of the active ingredient per unit dose.

19. The pharmaceutical composition according to claim 18, wherein the pharmaceutical composition is in a form of tablets, and each tablet comprises 152.4 mg of the active ingredient or comprises 125 mg of a free base of the active ingredient.

20. A method for treating coronavirus-induced diseases, comprising administrating the pharmaceutical composition according to claim 10 to a subject, wherein the coronavirus is 2019-nCoV.

* * * * *

(12) EX PARTE REEXAMINATION CERTIFICATE (13179th)
United States Patent
Wei et al.

(10) Number: US 11,655,240 C1
(45) Certificate Issued: Feb. 13, 2026

(54) CRYSTAL FORM OF COMPOUND AND FUMARIC ACID, PHARMACEUTICAL COMPOSITION AND METHOD FOR TREATING CORONAVIRUS-INDUCED DISEASES

(71) Applicants: BEIJING GRAND JOHAMU PHARMACEUTICAL COMPANY, LTD., Beijing (CN); NANJING GRITPHARMACO., LTD., NanJing (CN)

(72) Inventors: Weiye Wei, Beijing (CN); Jiannan Yang, Beijing (CN); Xiaotao Wu, Beijing (CN); Taotao Zhao, Beijing (CN); Hao Wang, Beijing (CN); Chao Li, Beijing (CN); Lei Qu, Beijing (CN); Bin Wang, Beijing (CN)

(73) Assignee: BEIJING GRAND JOHAMU PHARMACEUTICAL COMPANY, LTD., Beijing (CN)

Reexamination Request:
No. 90/019,368, Jan. 8, 2024

Reexamination Certificate for:
Patent No.: 11,655,240
Issued: May 23, 2023
Appl. No.: 17/964,389
Filed: Oct. 12, 2022

(30) Foreign Application Priority Data

May 10, 2022 (CN) .......... 202210500296.8
Jun. 9, 2022 (CN) .......... 202210644417.6
Sep. 15, 2022 (CN) .......... 202211119888.1

(51) Int. Cl.
*C07D 403/14* (2006.01)
*A61K 9/20* (2006.01)

(52) U.S. Cl.
CPC .......... *C07D 403/14* (2013.01); *A61K 9/2009* (2013.01); *A61K 9/2013* (2013.01); *A61K 9/2054* (2013.01); *A61K 9/2059* (2013.01); *C07B 2200/13* (2013.01)

(58) Field of Classification Search
None
See application file for complete search history.

(56) References Cited

To view the complete listing of prior art documents cited during the proceeding for Reexamination Control Number 90/019,368, please refer to the USPTO's Patent Electronic System.

*Primary Examiner* — Alan D Diamond

(57) ABSTRACT

The present disclosure provides a crystal form of a compound and fumaric acid, an active pharmaceutical ingredient and a pharmaceutical composition containing the same, and a method for treating coronavirus-induced diseases a using the same. In particular, the crystal form of the present disclosure comprises the compound of Formula (I) and fumaric acid, and the X-ray powder diffraction pattern of the crystal form obtained using Cu-Kα radiation includes at least three peaks selected from the group consisting of: $0.94°\pm0.2°$ $2\theta$, $19.06°\pm0.2°$ $2\theta$, $23.50°\pm0.2°$ $2\theta$, and $24.66°\pm0.2°$ $2\theta$. The crystal form of the present disclosure has a high purity, good stability, and a high melting point.

At the time of issuance and publication of this certificate, the patent remains subject to pending reissue application number 19/364,877 filed Oct. 21, 2025. The claim content of the patent may be subsequently revised if a reissue patent is issued from the reissue application.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-20 are cancelled.

\* \* \* \* \*